US011918441B2

(12) United States Patent
Xu et al.

(10) Patent No.: US 11,918,441 B2
(45) Date of Patent: Mar. 5, 2024

(54) HIGHLY EXTENSIBLE NONWOVEN WEBS AND ABSORBENT ARTICLES HAVING SUCH WEBS

(71) Applicant: The Procter & Gamble Company, Cincinnati, OH (US)

(72) Inventors: Han Xu, Cincinnati, OH (US); Meganne Frisch, Cincinnati, OH (US); Jaroslav Kohut, Znojmo (CZ); Sascha Kreisel, Frankfurt am Main (DE); Jiri Kummer, Znojmo (CZ); Fang Liu, Mason, OH (US); Michael J. Roddy, Cincinnati, OH (US); Patricia Rolon, Cincinnati, OH (US); Eric R. Schurdak, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 969 days.

(21) Appl. No.: 16/856,086

(22) Filed: Apr. 23, 2020

(65) Prior Publication Data
US 2020/0337910 A1 Oct. 29, 2020

Related U.S. Application Data

(60) Provisional application No. 62/837,927, filed on Apr. 24, 2019.

(51) Int. Cl.
*A61F 13/15* (2006.01)
*A61F 13/511* (2006.01)
(Continued)

(52) U.S. Cl.
CPC .... *A61F 13/15577* (2013.01); *A61F 13/5116* (2013.01); *A61F 13/51401* (2013.01);
(Continued)

(58) Field of Classification Search
CPC ............ A61F 13/15577; A61F 13/5116; A61F 13/51401; A61F 13/53; A61F 2013/15959;
(Continued)

(56) References Cited

U.S. PATENT DOCUMENTS 3,137,893 A    6/1964  Gelpke
3,559,648 A    2/1971  Mason, Jr.
(Continued)

FOREIGN PATENT DOCUMENTS

CA    2449437    1/2003
CA    2733472    9/2009
(Continued)

OTHER PUBLICATIONS

International Search Report and Written Opinion; Application Ser. No. PCT/US2020/028623; dated Jul. 21, 2020; 13 pages.
(Continued)

*Primary Examiner* — Jacqueline F Stephens
(74) *Attorney, Agent, or Firm* — Christian M. Best; Daniel Albrecht

(57) ABSTRACT

A highly extensible nonwoven web is provided. The highly extensible nonwoven web may include continuous multi-component fibers. The continuous multi-component fibers may include polypropylene, wherein the polypropylene has a crystallinity of less than about 41%. The polypropylene may have a melting temperature of less than about 161° C. The highly extensible nonwoven web may define a plurality of apertures. The apertures may be patterned. The highly extensible nonwoven web may form a portion of an absorbent article.

20 Claims, 23 Drawing Sheets

(51) Int. Cl.
*A61F 13/514* (2006.01)
*A61F 13/53* (2006.01)
*C08L 23/12* (2006.01)
*A61F 13/51* (2006.01)

(52) U.S. Cl.
CPC .............. *A61F 13/53* (2013.01); *C08L 23/12* (2013.01); *A61F 2013/15959* (2013.01); *A61F 2013/5103* (2013.01); *A61F 2013/51178* (2013.01); *A61F 2013/51411* (2013.01); *A61F 2013/51452* (2013.01); *A61F 2013/53062* (2013.01)

(58) Field of Classification Search
CPC .... A61F 2013/5103; A61F 2013/51178; A61F 2013/51411; A61F 2013/51452; A61F 2013/53062; C08L 23/12
See application file for complete search history.

(56) References Cited

U.S. PATENT DOCUMENTS

| | | |
|---|---|---|
| 3,655,501 A | 4/1972 | Tesch |
| 3,673,026 A | 6/1972 | Brown |
| 3,814,101 A | 6/1974 | Kozak |
| 3,849,845 A | 11/1974 | Obenaus |
| 3,860,003 A | 1/1975 | Buell |
| 3,886,941 A | 6/1975 | Duane et al. |
| 3,890,974 A | 6/1975 | Kozak |
| 3,911,173 A | 10/1975 | Sprague, Jr. |
| 3,929,135 A | 12/1975 | Thompson |
| 4,306,559 A | 12/1981 | Nishizawa et al. |
| 4,323,069 A | 4/1982 | Ahr et al. |
| 4,324,246 A | 4/1982 | Mullane et al. |
| 4,327,730 A | 5/1982 | Sorensen |
| 4,573,986 A | 3/1986 | Minetola et al. |
| 4,588,630 A | 5/1986 | Shimalla |
| 4,609,518 A | 9/1986 | Curro et al. |
| 4,610,678 A | 9/1986 | Goldman et al. |
| 4,623,340 A | 11/1986 | Luceri |
| 4,629,643 A | 12/1986 | Curro et al. |
| 4,637,819 A | 1/1987 | Ouellette et al. |
| 4,673,402 A | 6/1987 | Weisman et al. |
| 4,676,784 A | 6/1987 | Erdman et al. |
| 4,704,112 A | 11/1987 | Suzuki et al. |
| 4,741,941 A | 5/1988 | Englebert et al. |
| 4,780,352 A | 10/1988 | Palumbo et al. |
| 4,785,996 A | 11/1988 | Ziecker et al. |
| 4,798,604 A | 1/1989 | Carter |
| 4,834,735 A | 5/1989 | Alemany et al. |
| 4,840,829 A | 6/1989 | Suzuki et al. |
| 4,842,666 A | 6/1989 | Werenicz |
| 4,888,231 A | 12/1989 | Angstadt |
| 4,950,264 A | 8/1990 | Osborn, III et al. |
| 5,122,407 A | 6/1992 | Yeo et al. |
| 5,147,345 A | 9/1992 | Young et al. |
| 5,151,092 A | 9/1992 | Buell et al. |
| 5,234,423 A | 8/1993 | Alemany et al. |
| D349,159 S | 7/1994 | Huffman |
| H1377 H | 11/1994 | Perry |
| 5,369,858 A | 12/1994 | Gilmore et al. |
| 5,382,773 A | 1/1995 | Kurihara et al. |
| 5,433,715 A | 7/1995 | Tanzer et al. |
| 5,437,653 A | 8/1995 | Gilman et al. |
| D362,120 S | 9/1995 | Suskind et al. |
| 5,503,076 A | 4/1996 | Yeo |
| 5,518,801 A | 5/1996 | Chappell et al. |
| 5,520,673 A | 5/1996 | Yarbrough et al. |
| 5,536,555 A | 7/1996 | Zelazoski et al. |
| 5,571,096 A | 11/1996 | Dobrin et al. |
| 5,599,335 A | 2/1997 | Goldman et al. |
| 5,607,760 A | 3/1997 | Roe |
| 5,609,587 A | 3/1997 | Roe |
| 5,628,097 A | 5/1997 | Benson et al. |
| 5,628,737 A | 5/1997 | Dobrin et al. |
| 5,635,191 A | 6/1997 | Roe et al. |
| 5,643,588 A | 7/1997 | Roe et al. |
| 5,660,788 A | 8/1997 | Gray et al. |
| 5,704,101 A | 1/1998 | Majors et al. |
| 5,714,107 A | 2/1998 | Levy et al. |
| 5,718,698 A | 2/1998 | Dobrin et al. |
| 5,731,061 A | 3/1998 | Bezier |
| 5,735,984 A | 4/1998 | Hoff et al. |
| H1732 H | 6/1998 | Johnson |
| 5,770,144 A | 6/1998 | James et al. |
| 5,797,894 A | 8/1998 | Cadieux et al. |
| 5,804,021 A | 9/1998 | Abuto et al. |
| 5,824,352 A | 10/1998 | Yang et al. |
| 5,885,267 A | 3/1999 | Mishima et al. |
| 5,895,380 A | 4/1999 | Turi et al. |
| 5,897,541 A | 4/1999 | Uitenbroek et al. |
| 5,897,543 A | 4/1999 | Francis |
| 5,914,084 A | 6/1999 | Benson |
| 5,916,661 A | 6/1999 | Benson et al. |
| 5,919,177 A | 7/1999 | Georger et al. |
| 5,941,864 A | 8/1999 | Roe |
| 5,968,025 A | 10/1999 | Roe et al. |
| 5,990,376 A | 11/1999 | Inoue et al. |
| 5,998,696 A | 12/1999 | Schone |
| 6,015,936 A | 1/2000 | Takai et al. |
| 6,025,535 A | 2/2000 | Octavio |
| 6,030,372 A | 2/2000 | Buell et al. |
| 6,093,871 A | 7/2000 | Takai et al. |
| 6,114,595 A | 9/2000 | Moore et al. |
| 6,117,524 A | 9/2000 | Hisanaka et al. |
| 6,168,849 B1 | 1/2001 | Braverman et al. |
| D439,057 S | 3/2001 | Bissah et al. |
| 6,206,865 B1 | 3/2001 | Chen et al. |
| 6,228,462 B1 | 5/2001 | Lee et al. |
| 6,262,331 B1 | 7/2001 | Nakahata et al. |
| 6,270,623 B1 | 8/2001 | Goda et al. |
| 6,274,218 B1 | 8/2001 | Shimizu |
| 6,303,208 B1 | 10/2001 | Pelkie |
| 6,410,823 B1 | 6/2002 | Daley et al. |
| 6,452,064 B1 | 9/2002 | Thoren et al. |
| 6,454,747 B1 | 9/2002 | Shimada et al. |
| 6,468,626 B1 | 10/2002 | Takai et al. |
| 6,475,600 B1 | 11/2002 | Morman et al. |
| 6,479,130 B1 | 11/2002 | Takai et al. |
| 6,498,284 B1 | 12/2002 | Roe |
| 6,506,473 B1 | 1/2003 | Hisanaka et al. |
| 6,534,149 B1 | 3/2003 | Daley et al. |
| 6,610,391 B2 | 8/2003 | Molee |
| 6,632,504 B1 | 10/2003 | Gillespie et al. |
| 6,676,646 B2 | 1/2004 | Bast et al. |
| 6,713,159 B1 | 3/2004 | Blenke et al. |
| 6,716,441 B1 | 4/2004 | Osborne et al. |
| 6,840,928 B2 * | 1/2005 | Datta ................... A61F 13/62 604/385.22 |
| 6,849,065 B2 | 2/2005 | Schmidt et al. |
| 6,849,319 B2 | 2/2005 | Cree et al. |
| 6,916,969 B1 | 7/2005 | Helmfridsson et al. |
| 6,996,851 B2 | 2/2006 | Nordness et al. |
| 7,005,558 B1 | 2/2006 | Johansson et al. |
| 7,033,340 B1 | 4/2006 | Muscat et al. |
| 7,056,404 B2 | 6/2006 | McFall et al. |
| 7,118,639 B2 | 10/2006 | Delucia et al. |
| 7,371,919 B1 | 5/2008 | Busam et al. |
| D584,401 S | 1/2009 | Francoeur |
| 7,803,244 B2 | 9/2010 | Siqueira et al. |
| 7,806,880 B2 | 10/2010 | Roe et al. |
| 7,887,522 B2 | 2/2011 | Roe et al. |
| 7,967,801 B2 | 6/2011 | Hammons et al. |
| 8,022,267 B2 | 9/2011 | Hellstroem et al. |
| 8,186,296 B2 | 5/2012 | Brown et al. |
| 8,226,625 B2 | 7/2012 | Turner et al. |
| 8,226,626 B2 | 7/2012 | Turner et al. |
| 8,227,660 B2 | 7/2012 | Hara et al. |
| 8,231,595 B2 | 7/2012 | Turner et al. |
| 8,251,965 B2 | 8/2012 | Costea et al. |
| 8,388,594 B2 | 3/2013 | Turner et al. |
| 8,454,571 B2 | 6/2013 | Rezai et al. |
| 9,034,230 B2 | 5/2015 | Qureshi et al. |
| 9,044,353 B2 | 6/2015 | Stone et al. |

(56) References Cited

U.S. PATENT DOCUMENTS

| | | |
|---|---|---|
| 2001/0005540 A1 | 6/2001 | Hisanaka et al. |
| 2001/0053901 A1 | 12/2001 | Mizutani et al. |
| 2002/0013563 A1 | 1/2002 | Desai et al. |
| 2002/0028624 A1 | 3/2002 | Mizutani et al. |
| 2002/0034912 A1 | 3/2002 | Curro et al. |
| 2002/0062113 A1 | 5/2002 | Thomas et al. |
| 2002/0062115 A1 | 5/2002 | Wada et al. |
| 2002/0098764 A1 | 7/2002 | Mleziva et al. |
| 2002/0147435 A1 | 10/2002 | Coles et al. |
| 2002/0172371 A1 | 11/2002 | Baker et al. |
| 2002/0182371 A1 | 12/2002 | Soon et al. |
| 2002/0182396 A1 | 12/2002 | Delucia et al. |
| 2002/0193032 A1 | 12/2002 | Newkirk et al. |
| 2003/0003269 A1 | 1/2003 | Lee et al. |
| 2003/0004481 A1 | 1/2003 | Matsuoka et al. |
| 2003/0021951 A1 | 1/2003 | Desai et al. |
| 2003/0026945 A1 | 2/2003 | Lasko |
| 2003/0109839 A1 | 6/2003 | Costea et al. |
| 2003/0125687 A1 | 7/2003 | Gubernick et al. |
| 2003/0145517 A1 | 8/2003 | Miller |
| 2003/0149412 A1 | 8/2003 | Damaghi et al. |
| 2003/0187415 A1 | 10/2003 | Kudo et al. |
| 2003/0217945 A1 | 11/2003 | Kiene et al. |
| 2004/0043189 A1 | 3/2004 | Huang |
| 2004/0092902 A1 | 5/2004 | Schuehle et al. |
| 2004/0118811 A1 | 6/2004 | Stone et al. |
| 2004/0122396 A1 | 6/2004 | Maldonado et al. |
| 2004/0122404 A1 | 6/2004 | Meyer et al. |
| 2004/0127128 A1 | 7/2004 | Thomas |
| 2004/0127875 A1 | 7/2004 | Hammons et al. |
| 2004/0161586 A1 | 8/2004 | Cree et al. |
| 2004/0162536 A1 | 8/2004 | Becker et al. |
| 2004/0170813 A1 | 9/2004 | Digiacomantonio et al. |
| 2004/0181199 A1 | 9/2004 | Moberg-Alehammar et al. |
| 2004/0209042 A1 | 10/2004 | Peacock et al. |
| 2005/0027270 A1 | 2/2005 | Cree et al. |
| 2005/0096614 A1 | 5/2005 | Perez et al. |
| 2005/0131366 A1 | 6/2005 | Shimada |
| 2005/0148971 A1 | 7/2005 | Kuroda et al. |
| 2005/0202208 A1 | 9/2005 | Kelly |
| 2005/0244619 A1 | 11/2005 | Kauschke et al. |
| 2005/0256475 A1 | 11/2005 | Komatsu et al. |
| 2005/0288647 A1 | 12/2005 | Ellingson et al. |
| 2006/0019063 A1 | 1/2006 | Kelly |
| 2006/0069361 A1 | 3/2006 | Olson |
| 2006/0087053 A1 | 4/2006 | O'Donnell et al. |
| 2006/0107505 A1 | 5/2006 | Desai et al. |
| 2006/0129114 A1 | 6/2006 | Mason et al. |
| 2006/0141885 A1 | 6/2006 | Cobbs et al. |
| 2006/0142710 A1 | 6/2006 | Kigata et al. |
| 2006/0179539 A1 | 8/2006 | Harber |
| 2007/0032772 A1 | 2/2007 | Ehrnsperger et al. |
| 2007/0048498 A1 | 3/2007 | Cree |
| 2007/0073254 A1 | 3/2007 | Ponomarenko et al. |
| 2007/0088307 A1 | 4/2007 | Arizti et al. |
| 2007/0135787 A1 | 6/2007 | Raidel et al. |
| 2007/0191802 A1 | 8/2007 | Gubernick et al. |
| 2007/0256286 A1 | 11/2007 | Ngai |
| 2008/0138574 A1 | 6/2008 | Maschino et al. |
| 2008/0249494 A1 | 10/2008 | Digiacomantonio et al. |
| 2008/0294135 A1 | 11/2008 | Hara et al. |
| 2008/0294138 A1 | 11/2008 | Andersson et al. |
| 2008/0312622 A1 | 12/2008 | Beruda et al. |
| 2009/0030390 A1 | 1/2009 | Hammons et al. |
| 2009/0030391 A1 | 1/2009 | Hammons et al. |
| 2009/0082746 A1 | 3/2009 | Thomas et al. |
| 2009/0104831 A1 | 4/2009 | Bornemann et al. |
| 2009/0131896 A1 | 5/2009 | Ebitsuka et al. |
| 2009/0157021 A1 | 6/2009 | Sullivan et al. |
| 2009/0191779 A1 | 7/2009 | Cree |
| 2009/0233046 A1 | 9/2009 | Iulianetti |
| 2009/0247978 A1 | 10/2009 | Boissier |
| 2009/0259208 A1 | 10/2009 | Hellstrom et al. |
| 2009/0299316 A1 | 12/2009 | Seyler |
| 2010/0004615 A1 | 1/2010 | Boissier |
| 2010/0019415 A1 | 1/2010 | Stone et al. |
| 2010/0035014 A1 | 2/2010 | Hammons et al. |
| 2010/0036338 A1 | 2/2010 | Hammons et al. |
| 2010/0036346 A1 | 2/2010 | Hammons et al. |
| 2010/0100067 A1 | 4/2010 | Pugliese, III |
| 2010/0107396 A1 | 5/2010 | Yagyu et al. |
| 2010/0130952 A1 | 5/2010 | Murai |
| 2010/0164733 A1 | 7/2010 | Ales et al. |
| 2010/0196653 A1 | 8/2010 | Curro et al. |
| 2010/0233438 A1 | 9/2010 | Stone et al. |
| 2010/0280471 A1 | 11/2010 | Shah |
| 2010/0330326 A1 | 12/2010 | Turner et al. |
| 2011/0024940 A1 | 2/2011 | Khalid et al. |
| 2011/0046592 A1 | 2/2011 | Nishikawa et al. |
| 2011/0073513 A1 | 3/2011 | Weisman et al. |
| 2011/0106036 A1 | 5/2011 | Staahl et al. |
| 2011/0184370 A1 | 7/2011 | Seyler et al. |
| 2011/0196330 A1 | 8/2011 | Hammons et al. |
| 2011/0264064 A1 | 10/2011 | Arora et al. |
| 2011/0305870 A1 | 12/2011 | Curro et al. |
| 2011/0319853 A1 | 12/2011 | Yamashita et al. |
| 2012/0003423 A1 | 1/2012 | Cree et al. |
| 2012/0035566 A1 | 2/2012 | Sagisaka et al. |
| 2012/0095426 A1 | 4/2012 | Visscher et al. |
| 2012/0177886 A1 | 7/2012 | Kanya et al. |
| 2012/0273990 A1 | 11/2012 | O'Donnell et al. |
| 2012/0282436 A1 | 11/2012 | Coe et al. |
| 2012/0295060 A1 | 11/2012 | Mullane |
| 2012/0296304 A1 | 11/2012 | Choo et al. |
| 2013/0012898 A1 | 1/2013 | Bergendahl et al. |
| 2013/0139666 A1 | 6/2013 | Raidel et al. |
| 2013/0226122 A1 | 8/2013 | Roe et al. |
| 2014/0031779 A1 | 1/2014 | Hammons et al. |
| 2014/0087130 A1 | 3/2014 | Seyler et al. |
| 2014/0121624 A1 | 5/2014 | Kirby et al. |
| 2014/0148774 A1 | 5/2014 | Brown et al. |
| 2014/0151934 A1 | 6/2014 | Thomas et al. |
| 2014/0163500 A1 | 6/2014 | Roe et al. |
| 2014/0163506 A1 | 6/2014 | Roe et al. |
| 2014/0163511 A1 | 6/2014 | Roe et al. |
| 2014/0228795 A1 | 8/2014 | Castanares et al. |
| 2014/0296809 A1 | 10/2014 | Hammons et al. |
| 2014/0296815 A1 | 10/2014 | Takken et al. |
| 2014/0303581 A1 | 10/2014 | Karlsson |
| 2014/0324009 A1 | 10/2014 | Lee et al. |
| 2014/0336605 A1 | 11/2014 | Hardie et al. |
| 2015/0099086 A1 | 4/2015 | Kim et al. |
| 2015/0209189 A1 | 7/2015 | Mullane |
| 2015/0250663 A1 | 9/2015 | Wagner et al. |
| 2015/0283001 A1 | 10/2015 | Arizti et al. |
| 2015/0283003 A1 | 10/2015 | Rosati et al. |
| 2015/0322605 A1* | 11/2015 | Chester ............ A61F 13/15577 |
| | | 264/103 |
| 2016/0113826 A1 | 4/2016 | Liu et al. |
| 2016/0129626 A1 | 5/2016 | Arora et al. |
| 2016/0136010 A1 | 5/2016 | Roe et al. |
| 2016/0136014 A1* | 5/2016 | Arora ................ A61F 13/5123 |
| | | 428/137 |
| 2016/0136016 A1 | 5/2016 | Mullane et al. |
| 2016/0168509 A1 | 6/2016 | Hitchcock et al. |
| 2016/0168510 A1 | 6/2016 | Tasker et al. |
| 2016/0168511 A1 | 6/2016 | Hitchcock et al. |
| 2017/0151103 A1 | 6/2017 | Bianchi et al. |
| 2019/0105209 A1* | 4/2019 | Erdem ................ A61F 13/565 |

FOREIGN PATENT DOCUMENTS

| | | |
|---|---|---|
| CN | 2897211 | 5/2007 |
| CN | 202724134 | 11/2009 |
| CN | 201505226 | 6/2010 |
| CN | 201855363 | 6/2011 |
| CN | 102673030 | 9/2012 |
| CN | 101940514 | 12/2013 |
| CN | 103432970 A | 12/2013 |
| DE | 2806401 | 8/1979 |
| DE | 4106295 | 9/1992 |
| DE | 19647459 | 5/1998 |
| DE | 19846857 | 3/2000 |
| EP | 165807 | 12/1985 |

(56) References Cited

FOREIGN PATENT DOCUMENTS

| | | |
|---|---|---|
| EP | 172025 | 2/1986 |
| EP | 359501 | 3/1990 |
| EP | 495212 | 7/1992 |
| EP | 535579 | 4/1993 |
| EP | 589224 | 3/1994 |
| EP | 749737 | 12/1996 |
| EP | 749738 | 12/1996 |
| EP | 749740 | 12/1996 |
| EP | 545423 | 8/1997 |
| EP | 934737 | 8/1999 |
| EP | 749736 | 1/2000 |
| EP | 983758 | 3/2000 |
| EP | 1040807 | 10/2000 |
| EP | 749739 | 11/2000 |
| EP | 1086676 | 3/2001 |
| EP | 710472 | 4/2001 |
| EP | 1066006 | 5/2003 |
| EP | 1022007 | 3/2006 |
| EP | 2347872 | 1/2015 |
| GB | 2103933 | 9/1985 |
| GB | 2225724 | 7/1992 |
| GB | 2296464 | 7/1996 |
| GB | 2310606 | 9/1999 |
| JP | 03186261 | 8/1991 |
| JP | 6038818 | 2/1994 |
| JP | 06280150 | 10/1994 |
| JP | 2587116 | 3/1997 |
| JP | 10272152 | 10/1998 |
| JP | 2790875 | 12/1998 |
| JP | 2005040235 | 2/2005 |
| JP | 2005245789 | 9/2005 |
| JP | 2008006272 | 1/2008 |
| JP | 2009050621 | 3/2009 |
| JP | 2009172354 | 8/2009 |
| JP | 4357591 | 11/2009 |
| JP | 2010269029 | 12/2010 |
| JP | 2011078477 | 4/2011 |
| JP | 2011135979 | 7/2011 |
| JP | 2011239835 | 12/2011 |
| JP | 2012050548 | 3/2012 |
| KR | 2001064584 | 7/2001 |
| WO | WO 91/10415 | 7/1991 |
| WO | WO 93/11726 | 6/1993 |
| WO | WO 93/15701 | 8/1993 |
| WO | WO 95/13773 | 5/1995 |
| WO | WO 95/17867 | 7/1995 |
| WO | WO 96/10481 | 4/1996 |
| WO | WO 96/11107 | 4/1996 |
| WO | WO 96/19313 | 6/1996 |
| WO | WO 97/02133 | 1/1997 |
| WO | WO 97/03818 | 2/1997 |
| WO | WO 1997/09020 | 3/1997 |
| WO | WO 1997/11661 | 4/1997 |
| WO | WO 1999/030660 | 6/1999 |
| WO | WO9939671 | 8/1999 |
| WO | WO 2000/001334 | 1/2000 |
| WO | WO 2000/028929 | 5/2000 |
| WO | WO 2000/062826 | 10/2000 |
| WO | WO 2001/072251 | 10/2001 |
| WO | WO 2002/100632 | 12/2002 |
| WO | WO 2003/015681 | 2/2003 |
| WO | WO03024706 | 3/2003 |
| WO | WO 2003/071019 | 8/2003 |
| WO | WO 2004/009009 | 1/2004 |
| WO | WO 2004/098474 | 11/2004 |
| WO | WO 2007/001320 | 1/2007 |
| WO | WO 2000/037249 | 6/2009 |
| WO | WOI 2011/080643 | 7/2011 |
| WO | WO 2012/014957 | 2/2012 |
| WO | WO 2012/052172 | 4/2012 |
| WO | WO 2013/091150 | 6/2013 |
| WO | WO 2013/147222 | 10/2013 |
| WO | 2016100477 A1 | 6/2016 |
| WO | 2016100479 A1 | 6/2016 |
| WO | WO 2017/082834 | 5/2017 |

OTHER PUBLICATIONS

Schuck, Peter, Size-Distribution Analysis of Macromolecules by Sedimentation Velocity Ultracentrifugation and Lamm Equation Modeling, Biophysical Journal, Mar. 2000, pp. 1606-1619, vol. 78, No. 3.

ASTM D3954-94 (Reapproved 2010), Standard Test Method for Dropping Point of Waxes.

* cited by examiner

HIGHLY EXTENSIBLE NONWOVEN WEBS AND ABSORBENT ARTICLES HAVING SUCH WEBS

CROSS REFERENCE TO RELATED APPLICATION

This application claims the benefit, under 35 U.S.C. § 119(e), of U.S. Provisional Patent Application Ser. No. 62/837,927, filed Apr. 24, 2019, the entirety of which is incorporated herein by reference.

FIELD

The present disclosure is generally directed to highly extensible nonwoven webs, apertured highly extensible nonwoven webs, patterned apertured highly extensible nonwoven webs, and methods for making the same. The highly extensible nonwoven webs of the present disclosure may be used in absorbent articles, for example as topsheets, portions of belts, outer cover nonwoven materials, other absorbent article components, or components of other products.

BACKGROUND

Nonwoven webs are useful in many industries, including the medical and hygiene industries. In these industries, nonwoven webs may be incorporated into various components of absorbent articles, such as diapers, pants, adult incontinence articles, and feminine hygiene products. Nonwoven webs may experience strains during manufacturing and/or converting into a final product. These strains may be in the machine direction or the cross-machine direction. If the nonwoven webs are not properly extensible to accommodate these strains, fiber breakage may occur. Fiber breakage may have the undesirable effect of weakening the nonwoven webs. Broken fibers may also come loose from the web, potentially creating contamination of the manufacturing equipment and, in an absorbent article context, potentially causing fibers to stick to the skin of a wearer.

It may also be desirable to include value-added features, such as apertures and/or three-dimensional features to the nonwoven webs. Apertured nonwoven webs may also be useful in disposable absorbent articles, for example in an absorbent article topsheet context, as they may provide improved fluid handling properties. Apertures may be formed in nonwoven webs in many ways, such as pin aperturing, for example. Apertured nonwoven webs may also be produced by a process of overbonding (i.e., intermittently densifying) the nonwoven web prior to subjecting the nonwoven web to a cross-machine directional strain, causing at least some of the overbonds to at least partially rupture, forming apertures. Many value-added features, such as apertures, require a strain force exceeding 100%, and exceeding 150% in local areas of a nonwoven web. Subjecting a nonwoven web to a strain force sufficient to rupture overbonds, for example, may negatively impact the quality of the nonwoven web by causing fiber breakage in areas of the web that have not been overbonded. Additionally, the use of elastomeric polymers in nonwoven webs may be used to increase extensibility of the nonwoven web. However, due to the recovery behavior of elastomeric polymers, value-added features created in the nonwoven web tend to recover to their pre-processed state, and the value-added feature may be lost after processing.

Patterned (i.e. non-uniform and non-homogeneous) apertured nonwoven webs may also be produced by a process of overbonding and rupturing to form apertures. Patterning of the apertures may allow the nonwoven webs to have better depth perception, improved fluid handling properties, and/or aesthetically pleasing appearances relative to apertured webs that have uniform and homogenous apertures. Patterned apertured nonwoven webs may be especially susceptible to fiber breakage under a strain force due to the high strain force required and the localized strain that results from creating non-uniform and non-homogeneous apertures. Stated another way, in a cross-machine direction of a patterned apertured nonwoven web, there may be multiple lanes that do not have overbonds configured to form apertures, or that have only one or a few overbonds. As such, when the webs are stretched in the cross-machine direction, fiber breakage may occur in these lanes as the strain of the cross-directional force is not relieved by apertures rupturing. This may potentially lead to fiber breakage and fibers on skin.

Thus, nonwoven webs, and in some instances apertured nonwoven webs, or patterned apertured nonwoven webs, should be improved.

SUMMARY

To solve the problems advanced above, the present disclosure provides nonwoven webs that are highly extensible to accommodate strain forces, while still being sufficiently strong to inhibit neckdown of the nonwoven webs in a direction perpendicular to an applied stress. The present disclosure also provides nonwoven webs having improved resistance to fiber breakage under some strain forces required to convert the nonwoven webs into finished products, including forming value-added features, such as apertures, patterned apertures, and/or three-dimensional features. The nonwoven webs of the present disclosure may exhibit improved extensibility in the cross-machine direction to, for example, accommodate the strain force required to rupture the nonwoven web in overbonded areas and create apertures, while maintaining intact fibers in non-overbonded areas. This may allow for the creation of a stronger nonwoven web and reduced broken fibers and lint. Additionally, the nonwoven webs of the present disclosure may exhibit sufficient strength to at least inhibit excessive neckdown in the cross-machine direction, while under strain in the machine direction, during normal manufacturing processes. This may allow for reduced deformation of the nonwoven web during manufacturing processes, leading to efficient converting of the nonwoven web into consumer products, such as absorbent articles.

The present disclosure provides, in part, highly extensible nonwoven webs comprising staple or continuous multi-component fibers. The multi-component fibers of these nonwoven webs may comprise polypropylene, wherein the polypropylene component of the fibers has a crystallinity of between about 20% and about 41%. The polypropylene may also have a melting temperature of between about 130° C. and about 161° C.

The present disclosure provides, in part, a nonwoven topsheet for an absorbent article. The nonwoven topsheet may comprise a first nonwoven web comprising continuous multi-component fibers. The multi-component fibers may comprise polypropylene, wherein the polypropylene component of the fibers has a crystallinity of between about 20% and about 41%. The polypropylene may also have a melting temperature of between about 130° C. and about 161° C.

The nonwoven topsheet may define a plurality of apertures. The apertures may have a maximum measurable aperture area equivalent diameter of between about 1.5 mm and about 10 mm.

The present disclosure provides, in part, a low-lint nonwoven topsheet for an absorbent article. The low-lint nonwoven topsheet may comprise a first nonwoven web comprising continuous multi-component fibers. The multi-component fibers may comprise polypropylene, wherein the polypropylene component of the fibers has a crystallinity of between about 20% and about 41%. The polypropylene may also have a melting temperature of between about 130° C. and about 161° C. The nonwoven topsheet may define a plurality of apertures. The apertures may have a maximum measurable aperture area equivalent diameter of between about 1.5 mm and about 10 mm. The apertures may be patterned.

The present disclosure provides, in part, an absorbent article comprising a nonwoven topsheet. The nonwoven topsheet may comprise a first nonwoven web comprising continuous multi-component fibers. The multi-component fibers may comprise polypropylene, wherein the polypropylene component of the fibers has a crystallinity of between about 20% and about 41%. The polypropylene may also have a melting temperature of between about 130° C. and about 161° C.

The nonwoven topsheet may define a plurality of apertures. The apertures may have a maximum measurable aperture area equivalent diameter of between about 1.2 mm and about 10 mm.

The present disclosure provides, in part, absorbent articles comprising one or more highly extensible nonwoven webs. The one or more highly extensible nonwoven webs may form at least a portion of a topsheet, outer cover, leg cuff, waist cuff, an ear, a side panel, a belt, and/or any other component or components, for example.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Figure 1:
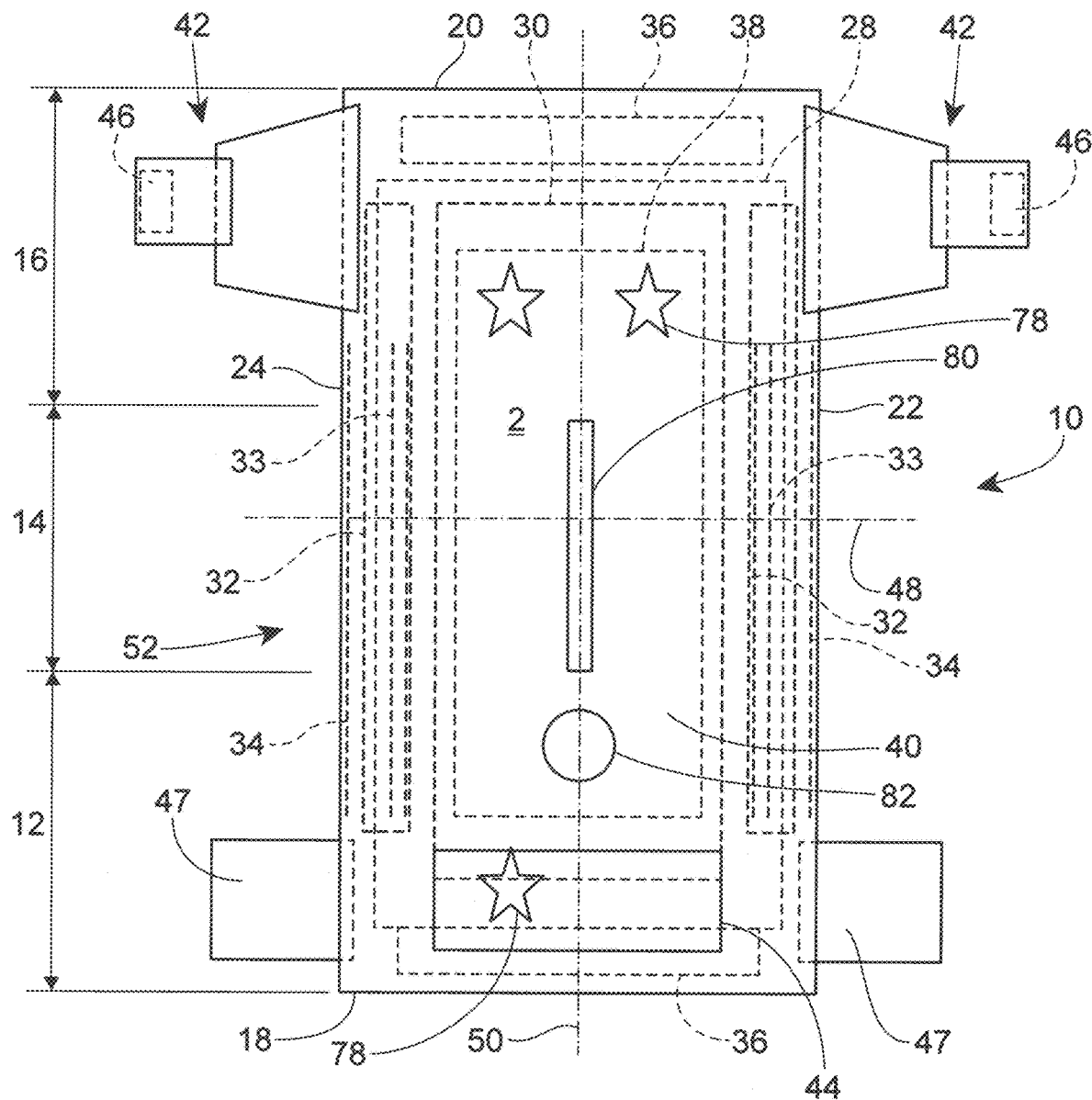
FIG. 1 is a plan view of an example absorbent article in the form of a taped diaper, garment-facing surface facing the viewer, in a flat laid-out state.

Various non-limiting forms of the present disclosure will now be described to provide an overall understanding of the principles of the structure, function, manufacture, and use of the highly extensible nonwoven webs and absorbent articles having such webs disclosed herein. One or more examples of these non-limiting forms are illustrated in the accompanying drawings. Those of ordinary skill in the art will understand that the highly extensible nonwoven webs and absorbent articles having such webs described herein and illustrated in the accompanying drawings are non-limiting examples. The features illustrated or described in connection with one non-limiting form may be combined with the features of other non-limiting forms. Such modifications and variations are intended to be included within the scope of the present disclosure.

As used herein, the term "cross direction" (CD) refers to a direction that is generally perpendicular to the machine direction.

As used herein, the term "machine direction" (MD) refers to the primary direction of material, strip of substrate, or article flow through a process.

As used herein, the term "nonwoven web" refers to a manufactured sheet, web, or batt of directionally or randomly orientated fibers bonded or otherwise joined together. The fibers may be of natural or man-made origin. Nonwoven webs can be formed by many processes such as meltblowing, spunbonding, solvent spinning, electrospinning, and airlaying. The basis weight of nonwoven webs is usually expressed in grams per square meter (g/m$^2$ or gsm). Multi-constituent fibers, such as bicomponent fibers, or any other suitable fibers, may also be used in forming the nonwoven webs.

As used herein, the term "overbond" refers to portions of a nonwoven web which have been subjected to localized heating and/or localized pressure to substantially consolidate the fibers of the nonwoven web into a densified and weakened film-like form. "Overbonding" and "overbonds" are distinguished from "primary bonds" and/or "point bonds" in that "primary bonds" and/or "point bonds" are relatively small points of consolidation of web fibers made during or soon after formation of the nonwoven web in order to hold the web structure together. "Primary bonds" and "point bonds" typically do not create apertures when strain is applied to the nonwoven web.

As used herein, the terms "patterned overbonds" "patterned apertures" or "patterned apertured nonwoven webs" refers to nonwoven webs defining a plurality of overbonds and/or apertures, wherein the overbonds and/or apertures have different sizes, shapes, and/or are spaced at varied distances from one another. These overbonds and/or apertures are non-uniform and non-homogeneous.

Nonwoven Webs

Nonwoven webs are useful in many fields, such as the hygiene field, the dusting and cleaning implement field, and the medical field, for example. In the hygiene filed, nonwoven webs are used in the absorbent article field, such as use as components of diapers, pants, adult incontinence products, tampons, liners, sanitary napkins, absorbent pads, bed pads, wipes, and various other products. Nonwoven webs may be used in absorbent articles as topsheets, outer cover nonwoven materials, portions of leg cuffs, acquisition materials, core wrap materials, portions of ears and side panels, portions of fastener tabs, portions of belts, and/or secondary topsheets, for example. The highly extensible nonwoven webs of the present disclosure may have particular application as a topsheet, a topsheet laminate, and/or an outer cover nonwoven material, for example.

Fiber Composition

The fibers of the highly extensible nonwoven webs of the present disclosure may comprise mono-component fibers or multi-component fibers, such as bi-component fibers or tri-component fibers, for example. Multi-component fibers, as used herein, means fibers comprising more than one chemical species or material (i.e., multi-constituent fibers). The fibers may comprise petroleum sourced resins, recycled resins, and/or bio-sourced resins, such as polylactic acid from Nature Works, polyethylene and/or polypropylene from Braskem, and polybutylene terephthalate from Lanxess. The fibers may have round, triangular, tri-lobal, or otherwise shaped cross-sections, for example. Often, the different polymer components have different melting temperatures, viscosities, glass transition temperatures, crystallinities, and/or crystallization rates. The multi-component fibers, such as bi-component fibers, may comprise sheath/core, side-by-side, islands in the sea, and/or eccentric configurations or may have other configurations. As an example, in the context of bi-component fibers, fibers comprising a core/sheath configuration may be comprised of a first polymer forming the core of the fiber, and a second polymer partially or completely surrounding the first polymer and forming the sheath of the fiber.

The fibers of the highly extensible nonwoven webs of the present disclosure may comprise crimped fibers. Crimped fibers may result when the different polymer components of multi-component fibers have different melting temperatures, viscosities, glass transition temperatures, crystallinities, and/or crystallization rates, and are disposed in an eccentric sheath/core or side-by-side configuration within the fibers. As the multi-component fibers cool after formation, a first polymer component may solidify and/or shrink at a faster rate than a second polymer component while the second polymer component may have sufficient rigidity to resist compression along a longitudinal fiber axis. The continuous fibers may deform and curl up when strain on the fiber is relieved, thereby causing what is known as "crimp" in the fibers. Crimp of the fibers aids in the softness and loft of a nonwoven web, which is consumer desirable Tensile Properties In addition to impacting the physical conformation of fibers (i.e., "crimped" fibers), the inventors have found that the selection of polymer components of the multi-component fibers may also impact the tensile properties of the fibers. The various components of a multi-component fiber may also impart different tensile properties to the nonwoven webs comprising the multi-component fibers. For example, one or more polymer component(s) of a multi-component fiber may impart rigidity and strength to the fiber, while another component or components may impart elasticity or extensibility. Fibers comprising polymer components with high levels of crystallinity, for example, may exhibit increased strength and increased resistance to stress forces. Fibers incorporating such polymer components may provide rigidity and strength to nonwoven webs comprising such fibers, allowing for a nonwoven web that is more easily handled during manufacturing processes. However, nonwoven webs comprising such fibers may also be brittle mand susceptible to fiber breakage under strain forces experienced during manufacturing and converting processes.

The inventors have surprisingly found that the selection of components used in multi-component fiber nonwoven webs may create highly extensible nonwoven webs that may also exhibit sufficient strength to at least partially resist a tendency to neckdown. Extensibility of a nonwoven web may be determined by the High Speed Tensile Test, as disclosed herein, which may reflect high strain rates a nonwoven web may experience during a value-added converting process. Briefly, engineering stress may be applied to a nonwoven web, and engineering strain exhibited by the nonwoven web is measured. The stress versus strain is plotted. The graph of stress versus strain may reveal certain properties of the nonwoven web, such as the yield point (the amount of stress at which a nonwoven web begins to deform plastically as opposed to elastically), the ultimate tensile strength (the maximum stress that a nonwoven web can withstand), and the fracture point (the point at which the fibers of the nonwoven web break). The conditions of the High Speed Tensile Test may be similar to the high strain rates encountered by a nonwoven web during value-added conversion processes.

A highly extensible nonwoven web may be beneficial to reduce fiber breakage under manufacturing conditions that may cause a nonwoven web to experience high strain forces, for example during the formation of apertures in a nonwoven web. In the absorbent article context, this may have the desirable effect of reducing the amount of broken fibers that stick to the skin of a wearer. Extensibility of a nonwoven web, however, may reduce the efficiency of converting a nonwoven web into a finished product due to a tendency of an extensible nonwoven web to neckdown, or narrow in a direction perpendicular to a direction of applied strain. Such a narrowing of a nonwoven web may cause the web to misalign with converting equipment or otherwise run inefficiently. The tendency of a nonwoven web to neckdown may be determined by the Neckdown Modulus Test, as described further herein.

According to the present disclosure, in the context of a multi-component fiber nonwoven web, the fibers may comprise a first polymer component having a first melting temperature and a second polymer component having a second melting temperature. The first polymer component may have a low crystallinity of between about 10% and about 41%, between about 15% and about 38%, between about 20% and about 35%, between about 25% and about 33%, or between about 28% and about 30%, for example, specifically reciting all 0.1% increments within the specified ranges and all ranges formed therein or thereby. Crystallinity may be measured in the fibers or nonwoven web comprising the fibers according to the Crystallinity Test disclosed herein. The first polymer component may have a melting temperature of between about 130° C. and about 161° C., between about 130° C. and about 155° C., or between about 135° C. and about 155° C., for example, specifically reciting all 0.1° C. increments within the specified ranges and all ranges formed therein or thereby. Without wishing to be bound by theory, it is believed that a polymer with low crystallinity may increase the extensibility of a fiber by increasing the ultimate tensile strength of the fiber. In one example, polypropylene with a crystallinity of between about 20% and about 41% may be the first polymer of a multi-component fiber nonwoven web. In another example, polyethylene terephthalate with a crystallinity of between about 20% and about 41% may be the first polymer of a multi-component fiber nonwoven web.

A second polymer component may have a high crystallinity of between about 40% and about 80%, between about 45% and about 75%, between about 50% and about 70%, or between about 55% and about 65%, for example, specifically reciting all 0.1% increments within the specified ranges and all ranges formed therein or thereby. Without wishing to be bound by theory, it is believed that a polymer with high crystallinity may increase the tensile strength of a fiber and the tensile strength of a nonwoven web comprising such a fiber. A nonwoven web with increase tensile strength may resist neckdown when exposed to strain. The second polymer component may optionally have a melting temperature that is the same as or lower than that of the first polymer component. In one example, polyethylene may be the second polymer component of a multi-component continuous fiber.

The second polymer component may have a speed of crystallization of between about 1300 ms and about 1360 ms, between about 1310 ms and about 1360 ms, between about 1320 mg and about 1355 ms, between about 1325 ms and about 1350 ms, or between about 1330 ms and about 1350 ms, specifically reciting all 0.1 ms increments within the specified ranges and all ranges formed therein or thereby. Speed of crystallization may be determined by the Flash DSC Test disclosed herein. Without wishing to be bound by theory, it is believed that a second polymer having a relatively faster speed of crystallization may act to further reduce the crystallinity of the first polymer component. It is believed that, when the second polymer crystallizes first, it protects the first polymer, leading to a more amorphous first polymer component.

In the context of a nonwoven web comprising continuous bi-component fibers, a first polymer component may be or may comprise polypropylene having a crystallinity of between about 20% and about 41%. The polypropylene may have a melting temperature of between about 130° C. and 161° C. The second polymer component may be or may comprise polyethylene having a crystallinity of between about 45% and about 75%. The polyethylene may have a speed of crystallization of between about 1300 ms and about 1360 ms. The polyethylene may have a melting temperature of between about 100° C. and about 140° C. The bi-component fibers may have a core/sheath configuration, wherein the polypropylene forms the core of the fiber, and wherein the polyethylene forms the sheath of the fiber, partially or completely surrounding the polypropylene core. Without wishing to be bound by theory, it is believed that the low-crystallinity polypropylene fiber core may be used to produce a nonwoven web with improved tensile properties, including increased extensibility. Additionally, it is believed that a sheath material with high crystallinity and a fast crystallization time partially or completely surrounding the core material during fiber spinning may protect the core material and achieve a more amorphous structure in the finished fiber.

In another example, a first polymer component of a bi-component continuous fiber may be polyethylene terephthalate (PET) having a crystallinity of between about 20% and about 41%. The second polymer component may be polyethylene. The continuous fibers may comprise a core/sheath structure where the PET may form the core of the fiber and the polyethylene may partially or completely surround the PET and form the sheath of the fiber.

The highly extensible nonwoven webs of the present disclosure may have an extensibility of between about 300% and about 500%, between about 305% and about 450%, between about 310% and about 425%, between about 315% and about 400%, or between about 320% and about 375%, specifically reciting all 1% increments within the specified ranges and all ranges formed therein or thereby, according to the High Speed Tensile Test. A highly extensible nonwoven web with an extensibility within the ranges stated above may be beneficial to reduce fiber breakage under manufacturing conditions that may cause a nonwoven web to experience high strain forces. Reduced fiber breakage may result in a stronger nonwoven web with reduced lint.

The highly extensible nonwoven webs of the present disclosure may have a neckdown modulus of between about 1300 N/m and about 1900 N/m, between about 1300 N/m and about 1800 N/m, or between about 1300 N/m and about 1750 N/m, specifically reciting all 1 N/m increments within the specified ranges and all ranges formed therein or thereby, according to the Neckdown Modulus Test. A highly extensible nonwoven web with a neckdown modulus within the ranges stated above may be beneficial and may be more easily handled during formation of value-added features and conversion into, for example, nonwoven components of an absorbent article.

General Continuous Fiber Nonwoven Formation Process

Many nonwoven webs are made from melt-spinnable polymers and are produced using a spunbond process. The term "spunbond" refers to a process of forming a nonwoven web from thin continuous fibers produced by extruding molten polymers from orifices of a spinneret. The continuous fibers are drawn as they cool. When multi-component fibers are desired, two or more polymer components are fed to the spinneret and extruded simultaneously. Quenching of the continuous fibers may be performed by blowing air or other fluid onto the continuous fibers from one side or multiple sides under the spinneret in one or more open or enclosed chambers. Quench air or fluid temperate, flow rate, and/or humidity may be controlled in one or more stages located along the continuous fibers. Continuous fiber speed of travel during quenching may be in range from about 1,000 m/min to about 8,000 m/min, for example, depending on the polymers selected. Air is the most common method of fiber attenuation in systems, such as mostly enclosed chambers developed by Reifenhauser GmbH, or by aspirators developed by Hills Inc., or inside Doncan systems developed by Lurgi GmbH. Mechanical methods, such as take-up rollers, or electrostatic methods may also be used for continuous fiber attenuation. After fiber attenuation, the continuous fibers are randomly laid on a moving porous member, such as a moving porous belt, such that the continuous fibers form an intermediate continuous fiber nonwoven web. The intermediate continuous fiber nonwoven web is subsequently bonded using one of several known techniques, such as thermal point bonding or through-fluid bonding, for example, to form the nonwoven web.

General Description of an Absorbent Article

Figure 2:
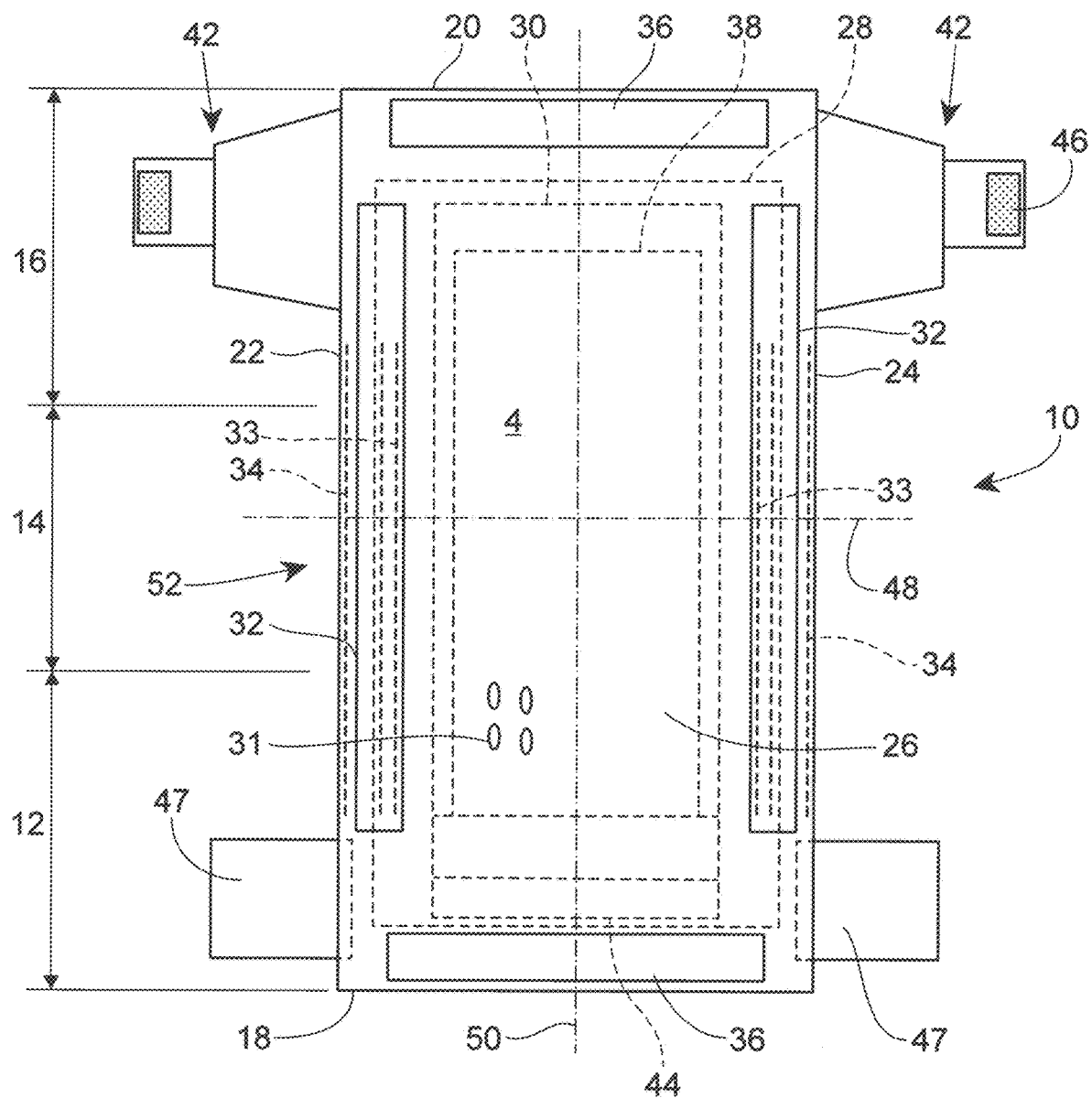
FIG. 2 is a plan view of the example absorbent article of FIG. 1, wearer-facing surface facing the viewer, in a flat laid-out state.
Figure 3:
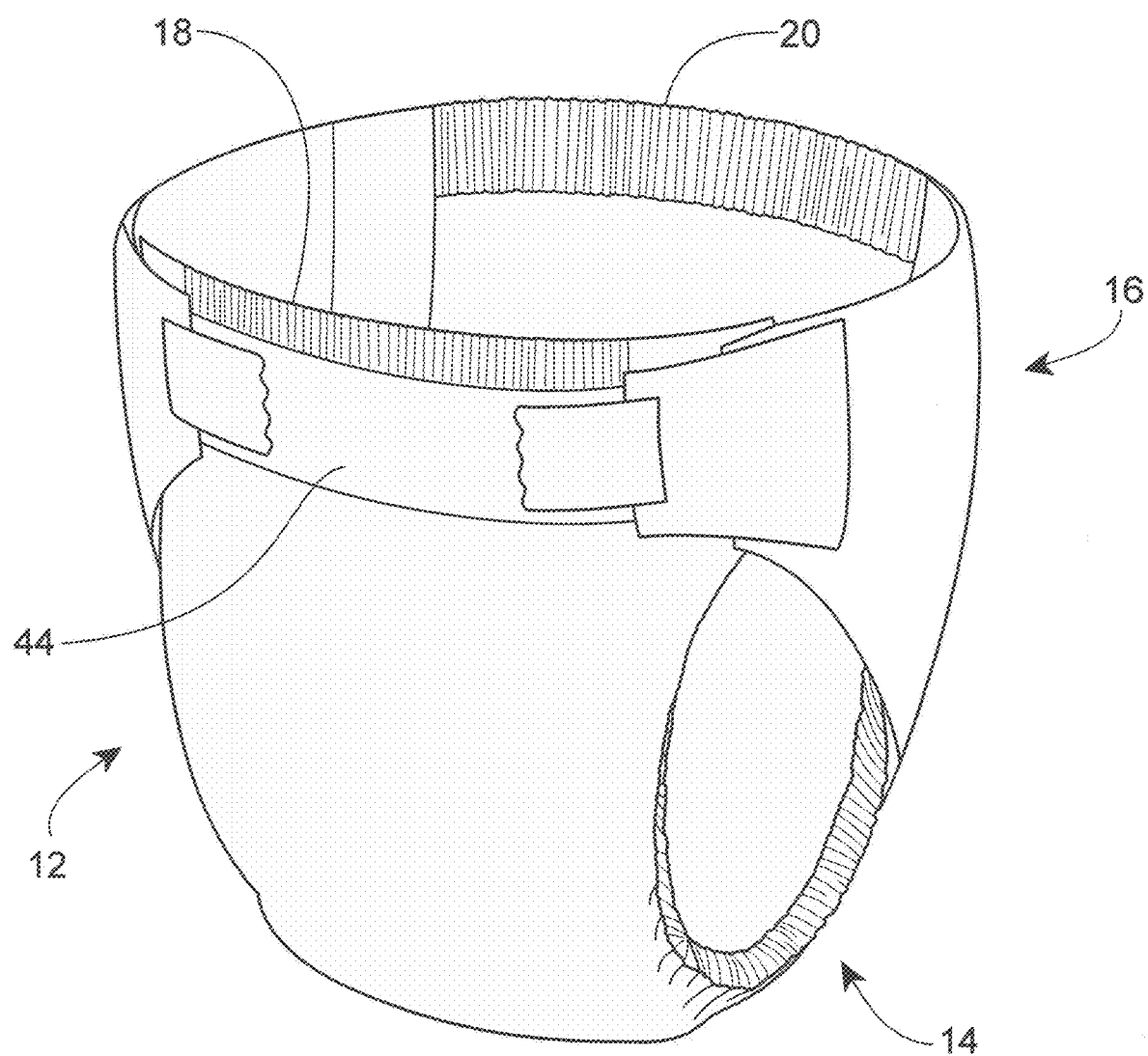
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover material 40, such as a nonwoven material, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
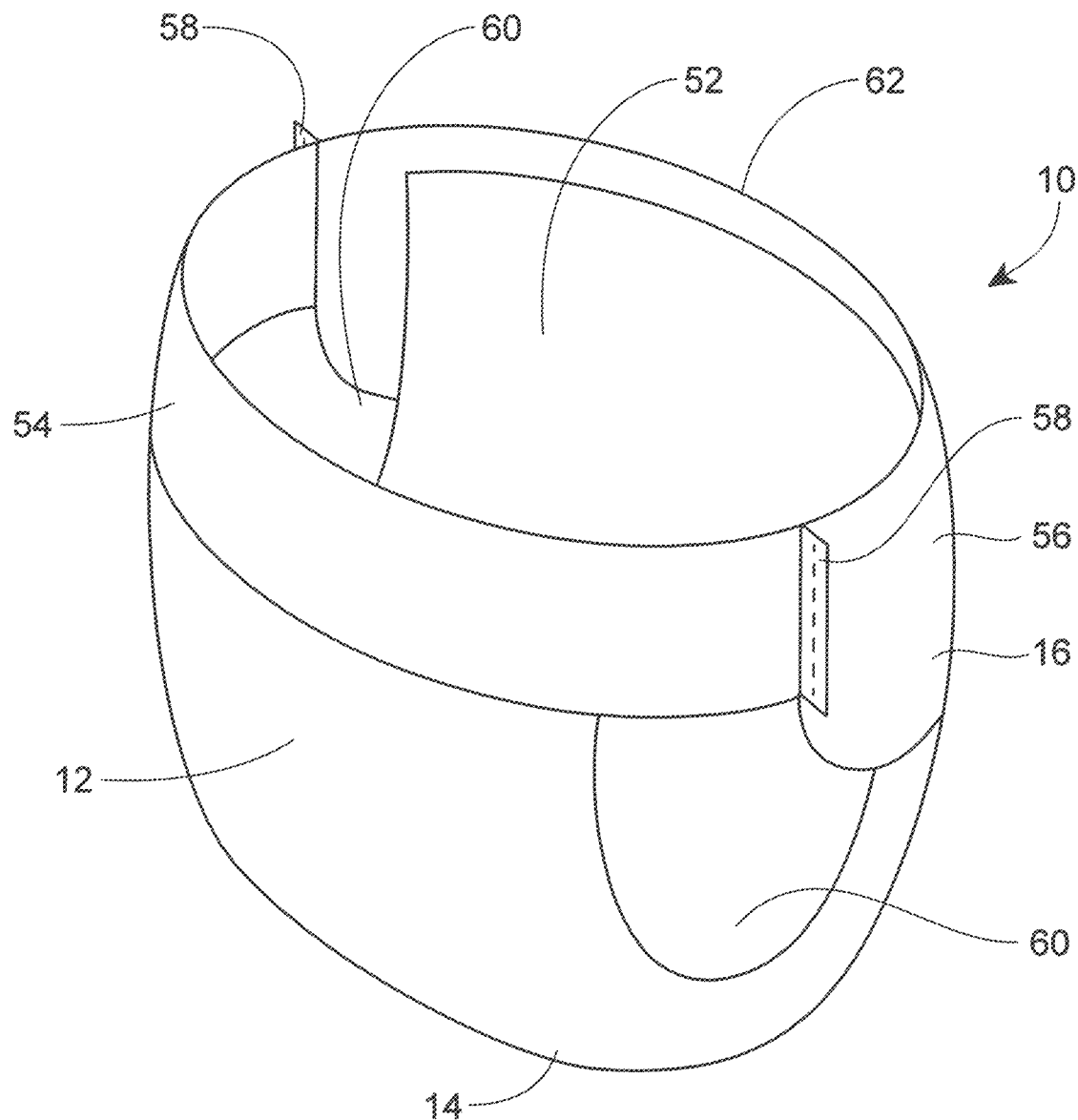
FIG. 4 is a front perspective view of an absorbent article in the form of a pant.
Figure 5:
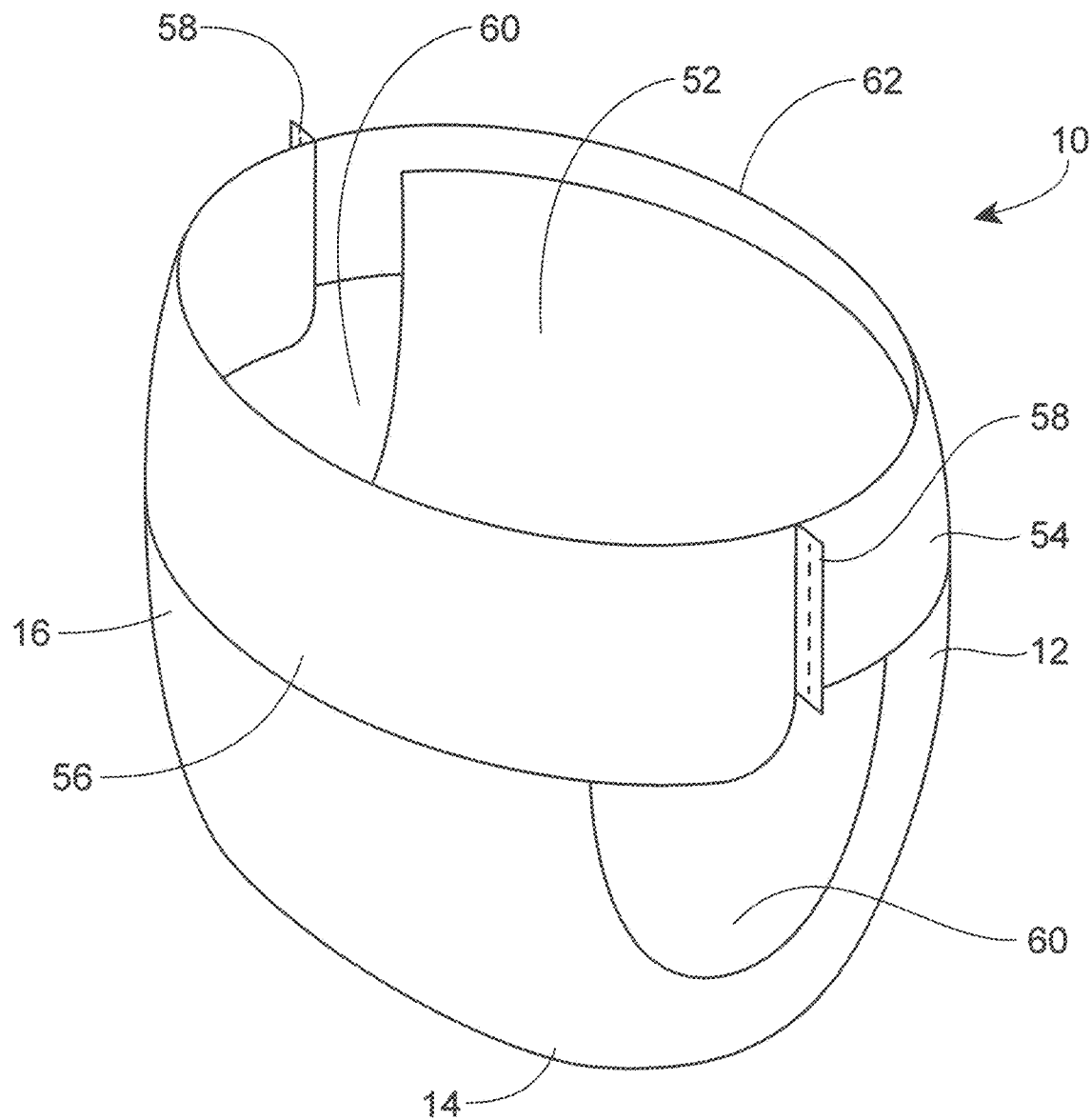
FIG. 5 is a rear perspective view of the absorbent article of FIG. 4.
Figure 6:
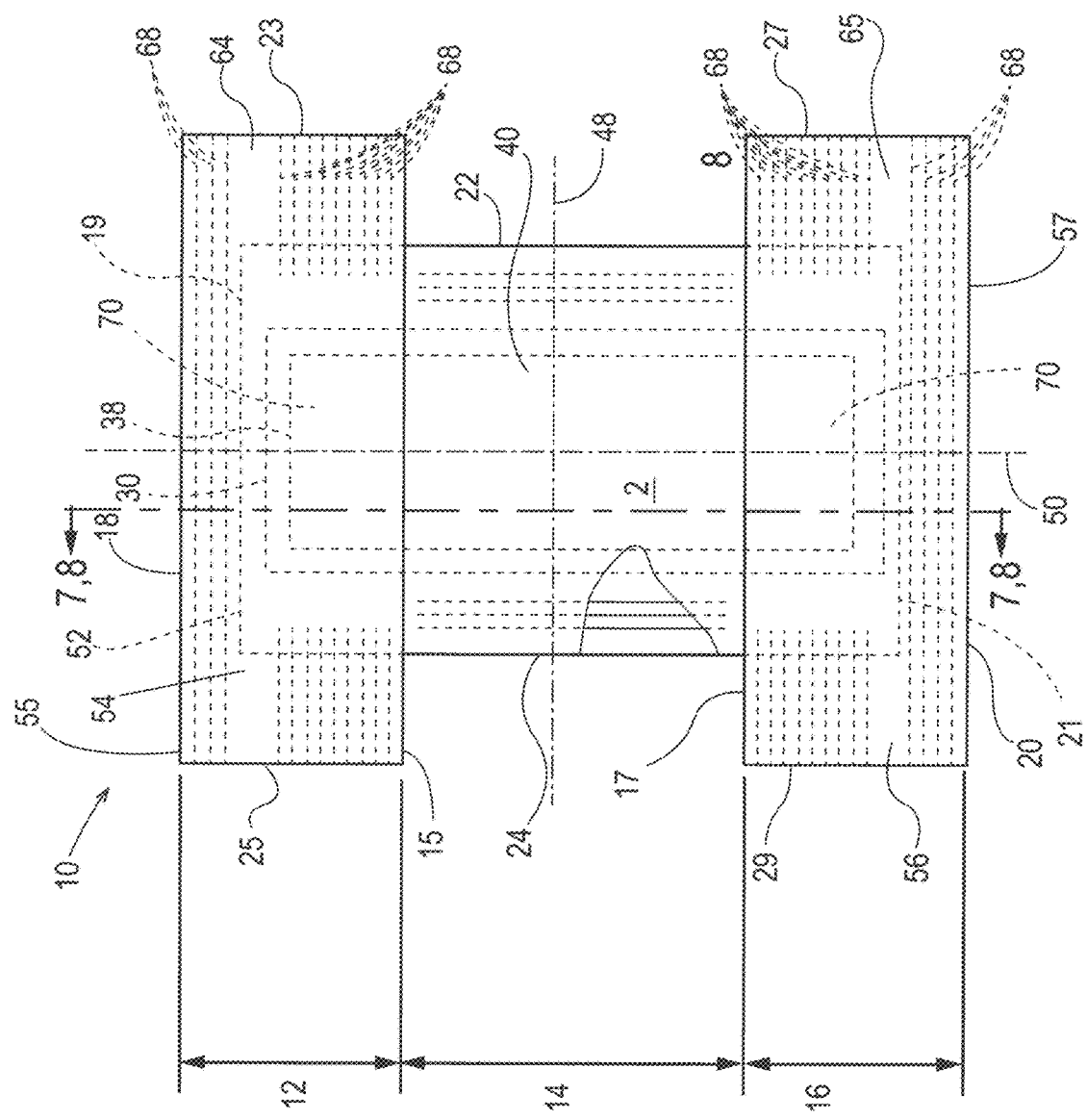
FIG. 6 is a plan view of the absorbent article of FIG. 4, laid flat, with a garment-facing surface facing the viewer.
Figure 7:
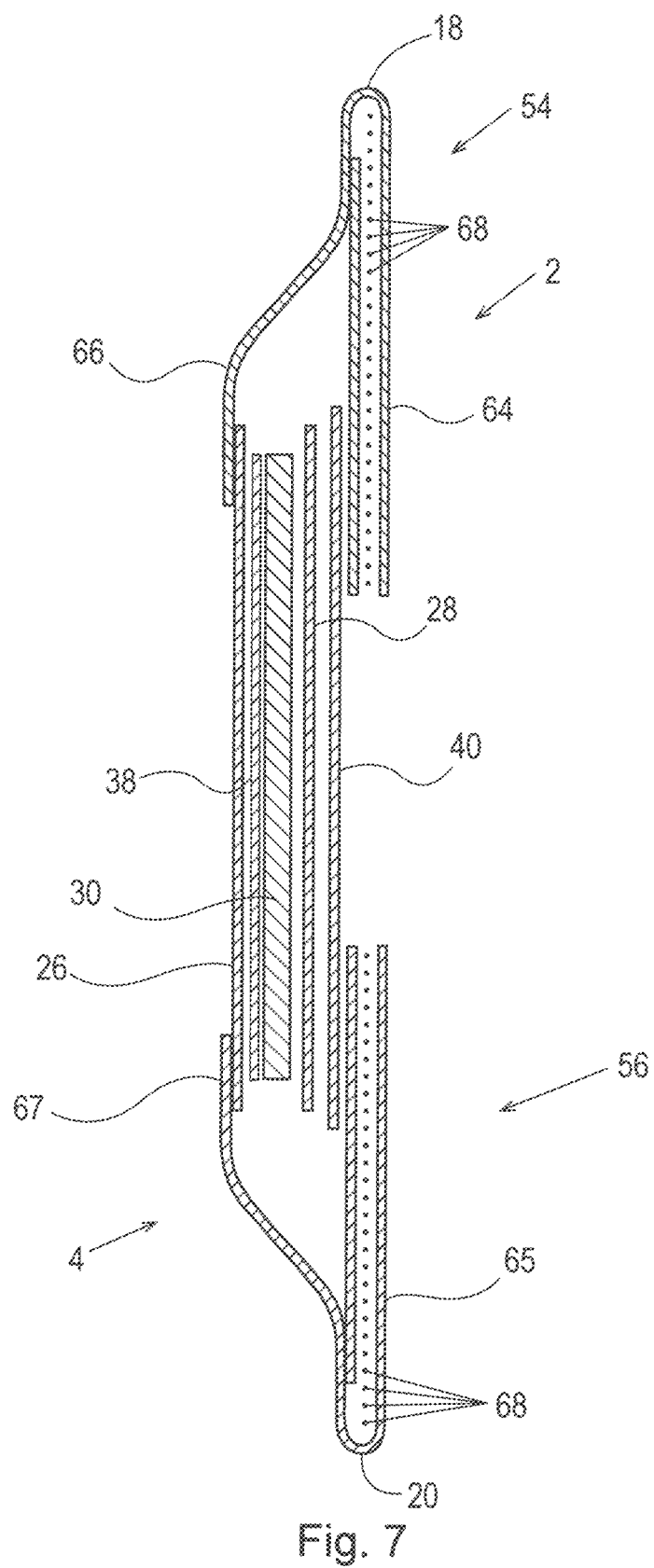
FIG. 7 is a cross-sectional view of the absorbent article taken about line 7-7 of FIG. 6.
Figure 8:
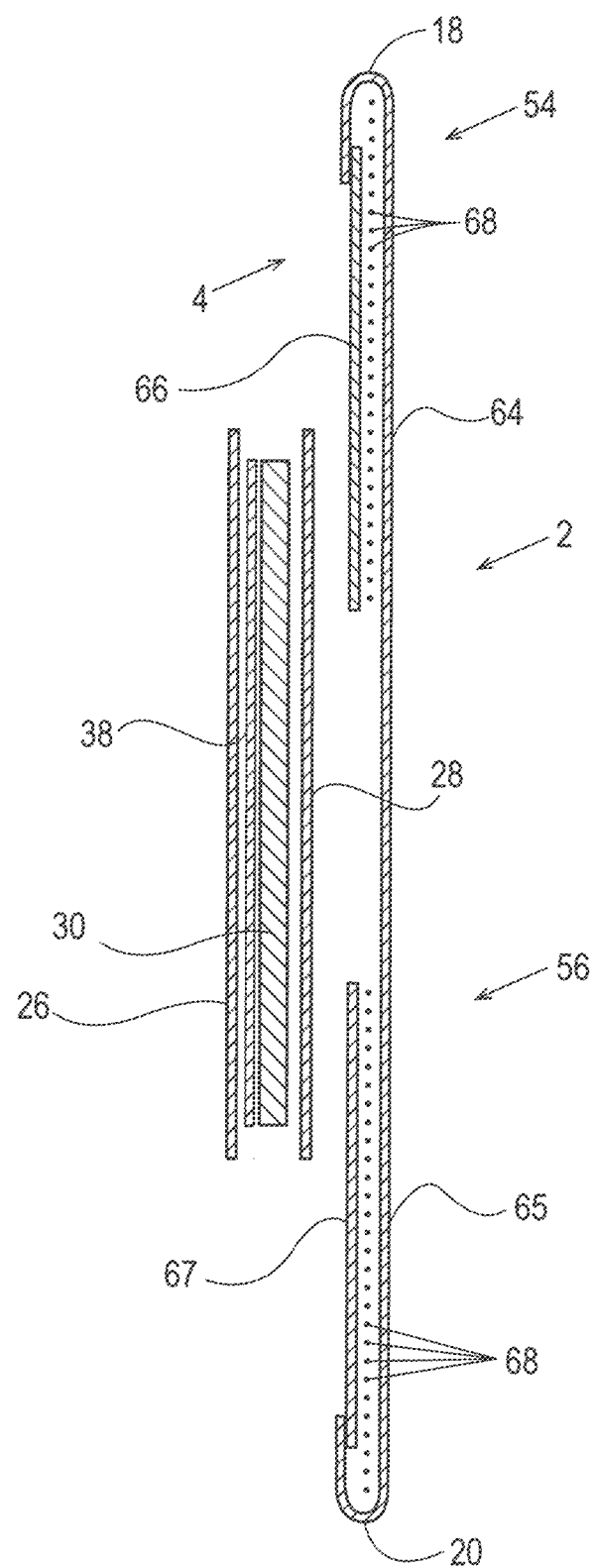
FIG. 8 is a cross-sectional view of the absorbent article taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

The highly extensible nonwoven webs of the present disclosure may be used as nonwoven portions of the front and back belts in an absorbent article.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 2, element 31), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al., and discussed further herein. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

According to the present disclosure, the topsheet may be low-lint. The topsheet may comprise a highly extensible nonwoven web comprising continuous multi-component fibers. The multi-component fibers of the nonwoven web may comprise polypropylene, wherein the polypropylene may have a crystallinity of between about 20% and about 41%, according to the Crystallinity Test Method disclosed herein. The polypropylene may optionally have a melting temperature of between about 110° C. and about 155° C. The multi-component fibers of the nonwoven may comprise polyethylene. In a core/sheath configuration, the polypropylene may comprise a core of the multi-component fibers, and a polyethylene sheath may partially or completely surround the polypropylene core. The nonwoven web may be joined to a second nonwoven web to form a laminate. The second nonwoven web may have the same structural and chemical properties as the nonwoven webs described herein. One of the nonwoven webs of the laminate topsheet may be hydrophilic and another of the nonwoven webs may be hydrophobic, for example.

The topsheet may define a plurality of apertures. The maximum measurable aperture area equivalent diameter may be between about 1.5 mm and about 10 mm, according to the Aperture Area Equivalent Diameter Test as disclosed herein. This may allow the topsheet to have better depth perception, improved fluid handling properties, and/or an aesthetically pleasing appearances. The perimeters, or portions thereof, of at least some of the apertures may comprise a melt lip. The topsheet may have an Effective Open Area of between about 7% and about 30%, according to the Effective Open Area Test disclosed herein.

The highly extensible nonwoven webs of the present disclosure may be used as nonwoven portions of, or the entirety of, the topsheet in an absorbent article.

Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Material

The outer cover nonwoven material (sometimes referred to as a backsheet nonwoven) 40 may comprise one or more nonwoven materials joined to the backsheet 28 and that covers the backsheet 28. The outer cover nonwoven material 40 forms at least a portion of the garment-facing surface 2 of the absorbent article 10 and effectively "covers" the backsheet 28 so that film is not present on the garment-facing surface 2. The outer cover nonwoven material 40 may comprise a bond pattern, apertures, and/or three-dimensional features. The highly extensible nonwoven webs of the present disclosure may form portions of, or all of, the outer cover nonwoven material 40. Patterned apertured nonwoven webs of the present invention may be used as outer cover nonwoven material as they may provide excellent contrast between apertured and non-apertured areas, allowing the pattern to be easily noticed.

Absorbent Core

Figure 9:
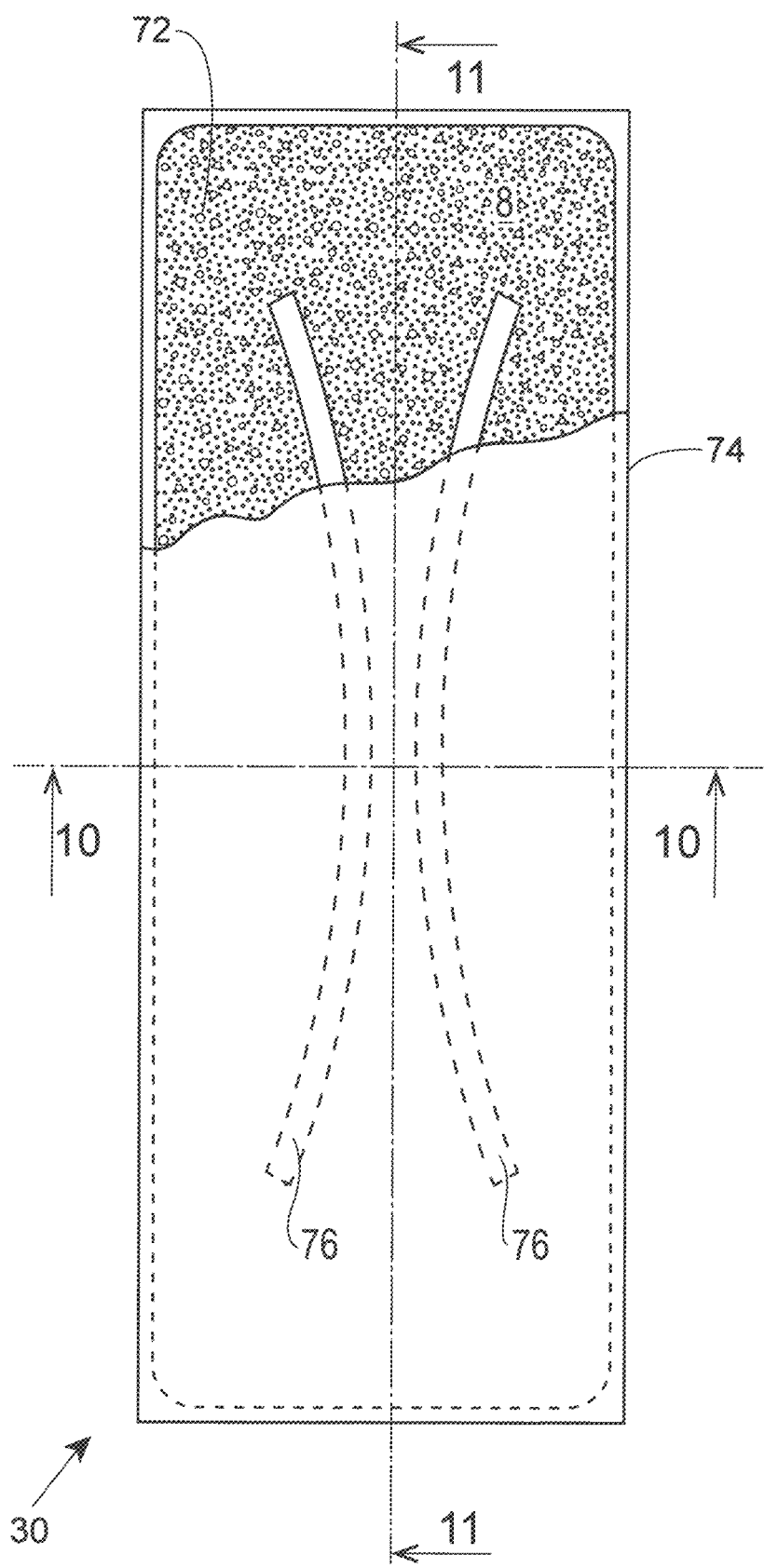
FIG. 9 is a plan view of an example absorbent core or an absorbent article.
Figure 10:
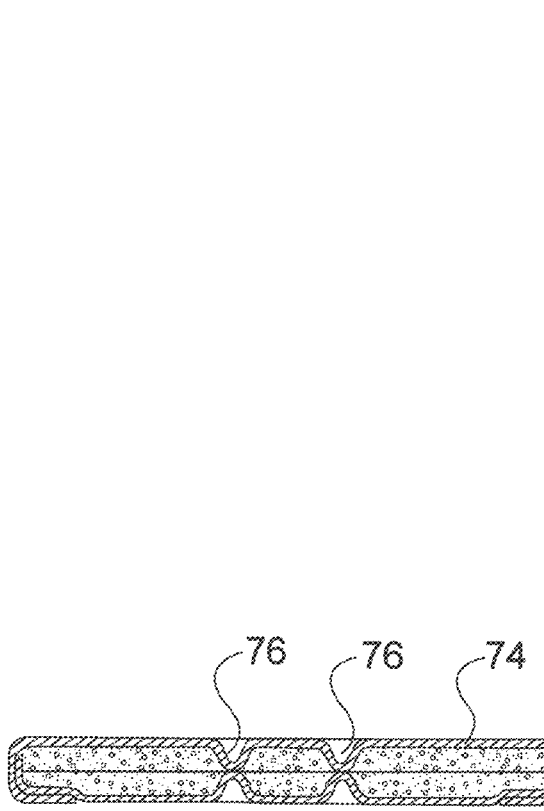
FIG. 10 is a cross-sectional view, taken about line 10-10, of the absorbent core of FIG. 9.
Figure 11:
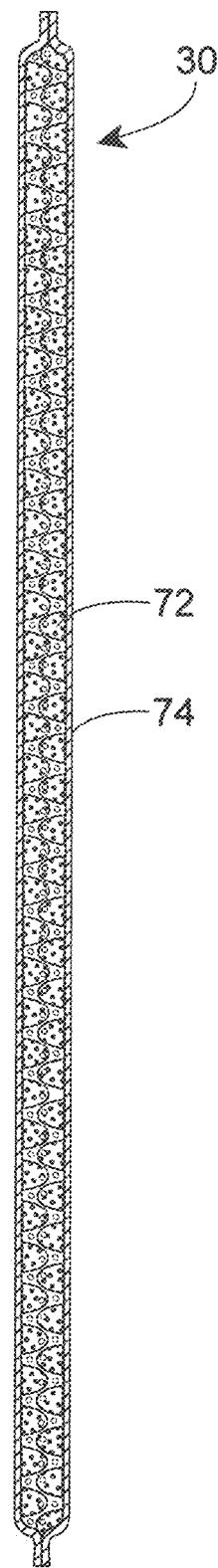
FIG. 11 is a cross-sectional view, taken about line 11-11, of the absorbent core of FIG. 10.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may be free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material and may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14. The highly extensible nonwoven webs of the present disclosure may form nonwoven portions of the barrier leg cuffs.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article. The highly extensible nonwoven webs of the present disclosure may form nonwoven portions of the elastic waistbands 36.

Acquisition Materials

Referring to FIGS. 1, 2, 7, and 8, one or more acquisition materials 38 may be present at least partially intermediate the topsheet 26 and the absorbent core 30. The acquisition materials 38 are typically hydrophilic materials that provide significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven material and as second acquisition material may comprise a cross-linked cellulosic material. The highly extensible nonwoven webs of the present disclosure may form nonwoven portions of, or all of, the acquisition material.

Landing Zone

Referring to FIGS. 1 and 2, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa. In other instances, a landing zone may not be provided and the outer cover nonwoven material 40 may function as a landing zone. The landing zone may be at least partially formed of the highly extensible nonwoven webs of the present disclosure.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material 40, the backsheet 28, and/or the topsheet 26) or may be discrete components attached to a chassis 52 of the absorbent article on a wearer-facing surface 4, on the garment-facing surface 2, or intermediate the two surfaces 4, 2. Nonwoven portions of the front and back ears may be formed of the highly extensible nonwoven webs of the present disclosure.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, AGM). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical nmarker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Sanitary Napkin

Figure 12:
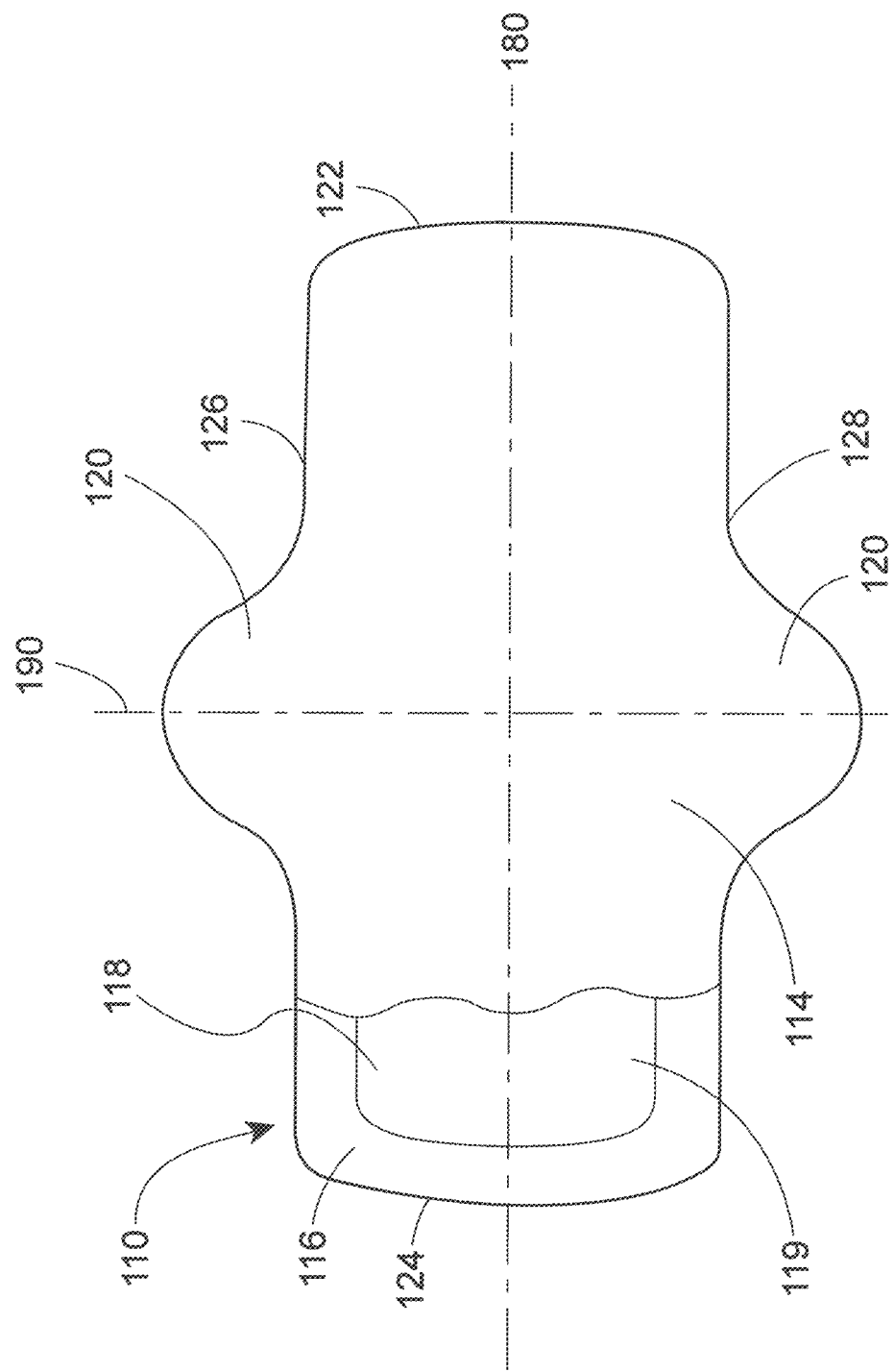
FIG. 12 is a plan view of an example absorbent article of the present disclosure that is a sanitary napkin.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art. The highly extensible nonwoven webs of the present disclosure may be used as nonwoven portions of a sanitary napkin.

Value-Added Nonwoven Webs

Multi-component continuous fiber nonwoven webs may be manufactured to include value-added features, such as apertures, patterned apertures, and/or other three-dimensional features. The creation of value-added features may require the application of tensile stress, causing a nonwoven web to experience significant tensile strain with very high strain rate, for example greater than 500 $s^{-1}$. The average tensile strain experienced by a nonwoven web during the creation of value-added features may exceed 100%.

The three-dimensional features may comprise ridges, projections, tufts, and/or domes, for example. The three-dimensional features may extend from either surface of the highly extensible nonwoven webs or both surfaces of the highly extensible nonwoven webs. The three-dimensional features may be used in nonwoven webs in combination with apertures or without apertures. One example of a nonwoven web having three-dimensional features is disclosed in U.S. Patent Application Publication No. 20150250662, published on Sep. 10, 2015. Another example of a nonwoven web having three-dimensional features is disclosed in U.S. Patent Application Publication No. 20180228668, published on Aug. 16, 2018.

As mentioned above, the highly extensible nonwoven webs may comprise apertures. Apertures may be formed in the highly extensible nonwoven webs of the present disclosure using any known method, including pin aperturing, for example. Apertures may also be produced by a process of overbonding (intermittently densifying) the nonwoven web prior to subjecting the nonwoven web to a cross-machine directional strain, causing at least some of the overbonds to at least partially rupture. Subjecting a nonwoven web to a strain force sufficient to rupture overbonds, however, may cause fiber breakage in non-overbonded areas of the nonwoven web. The highly extensible nonwoven webs of the present disclosure may overcome the issue of fiber breakage at high strain forces because the fibers comprising the nonwoven webs may have an increased ultimate tensile strength and resist breaking at higher strain forces as compared to conventional nonwoven webs.

Figure 13:
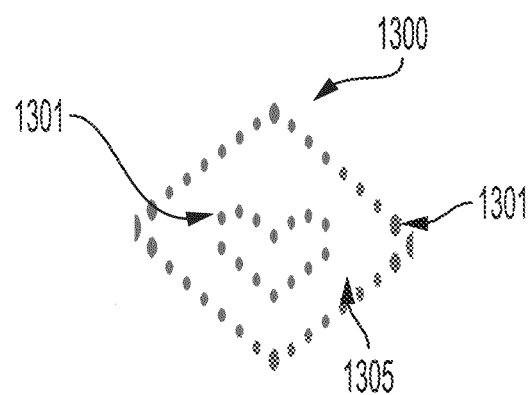
FIG. 13 represents a schematic illustration of a patterned aperture array for a patterned apertured nonwoven web, with apertures being black portions and land areas being white portions.
Figure 14:
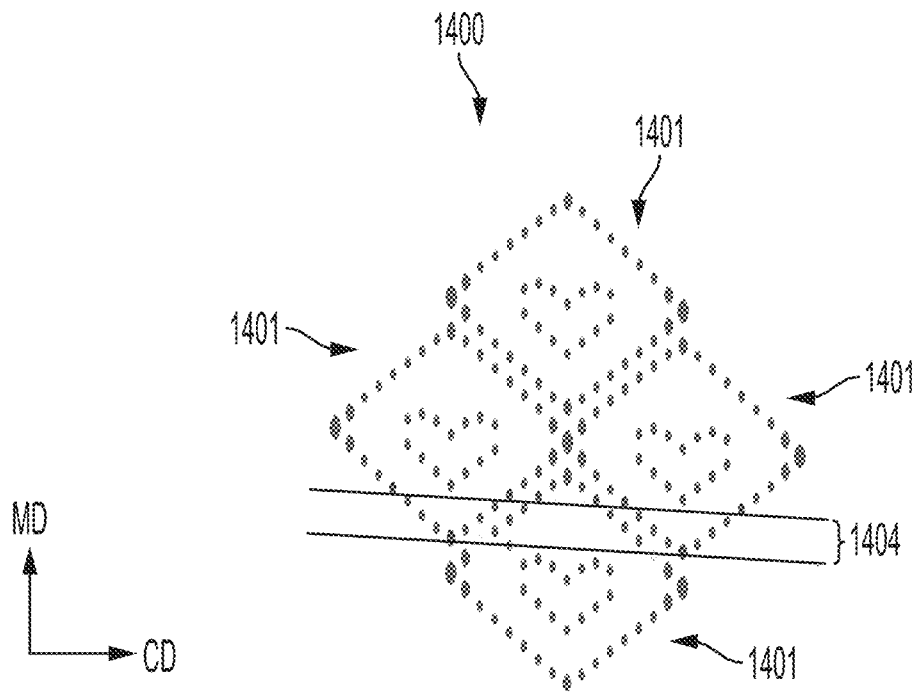
FIG. 14 represents a schematic illustration of a patterned aperture macro-array for a patterned apertured nonwoven web.

Patterned apertured nonwoven webs may be formed by a similar overbonding/rupturing process. However, due to the non-homogeneous and non-uniform placement of the apertures, patterned apertured nonwoven webs may experience even greater localized strain forces as compared to nonwoven webs comprising uniform and homogenous aperture patterns, for example greater than 1000 $s^{-1}$. The apertures may form a random, non-homogeneous pattern, or, as shown in FIG. 13, may be grouped in arrays of apertures. Referring to FIG. 13, apertures 1301 of an aperture array 1300 may be spaced such that a pattern emerges both in the apertures 1301 and also in the surrounding land area 1305. The aperture arrays 1300 may form a regular or recognizable shape, such as a heart shape, polygon, ellipse, arrow, chevron, and/or other shapes known in the pattern art. Referring to FIG. 14, the aperture arrays 1401 may be organized into "macro-arrays" 1400, having a higher order structure. There may be multiple lanes 1404 in the cross-machine direction that have only a few apertures relative to other lanes, no apertures, or smaller apertures. Therefore, the lanes 1404 may receive greater localized strain during the rupturing process because there are fewer (or no, or smaller) overbonds to rupture and relieve the strain. Therefore, the highly extensible nonwoven webs of the present disclosure may at least partially prevent fiber breakage within the land areas 1305 and the lanes 1404 in that their fibers have more extensibility and are less prone to breakage.

Figure 15:
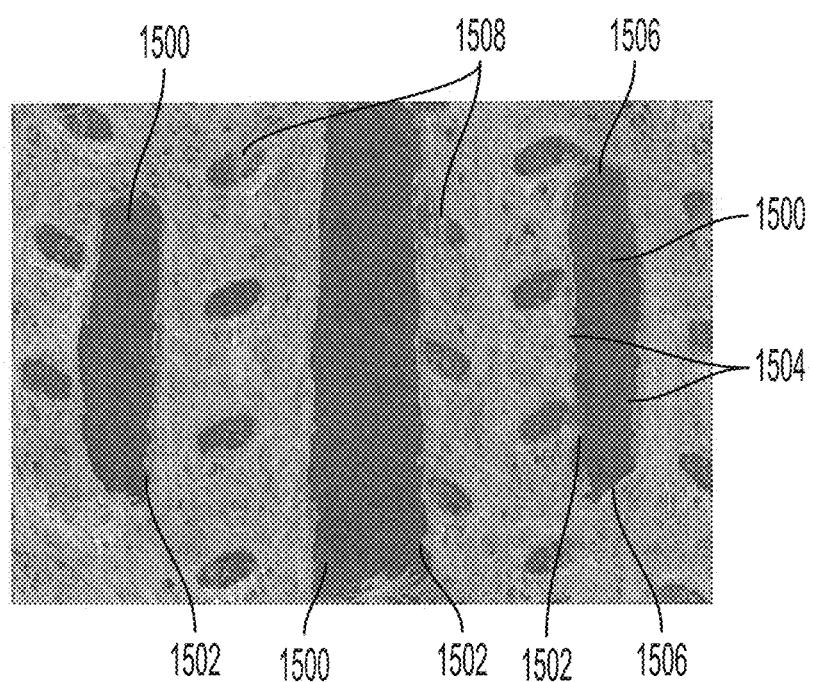
FIG. 15 is a photograph of a portion of a patterned apertured web comprising melt lip portions surrounding apertures.

Referring to FIG. 15, a portion of a patterned aperture web is illustrated. Portions of perimeters of at least portions of apertures 1500 in a patterned apertured web formed by an overbonding/rupturing process of the present disclosure may comprise one or more melt lips 1502. The melt lips 1502 may at least partially surround the apertures 1500. In various apertures, the melt lips 1502 may surround at least 25% of a perimeter of the apertures 1500 up to about 100% of the perimeter of the apertures 1500. In some instances, the melt lips 1502 may be formed on the lateral sides 1504 of the apertures 1500 and not on the leading or trailing edges 1506 of the apertures 1500. The melt lips are believed to be fused portions formed during the overbonding step and are believed to add strength and fiber holding power to the patterned apertured web and may also reduce lint formation. Primary bond sites 1508 used in the nonwoven web manufacturing process to hold the fibers together are also illustrated in FIG. 15. Without wishing to be bound by theory, it is believed that the lower melting temperature of at least one of the polymer components of the highly extensible nonwoven web is more favorable to forming melt lips.

Figure 16:
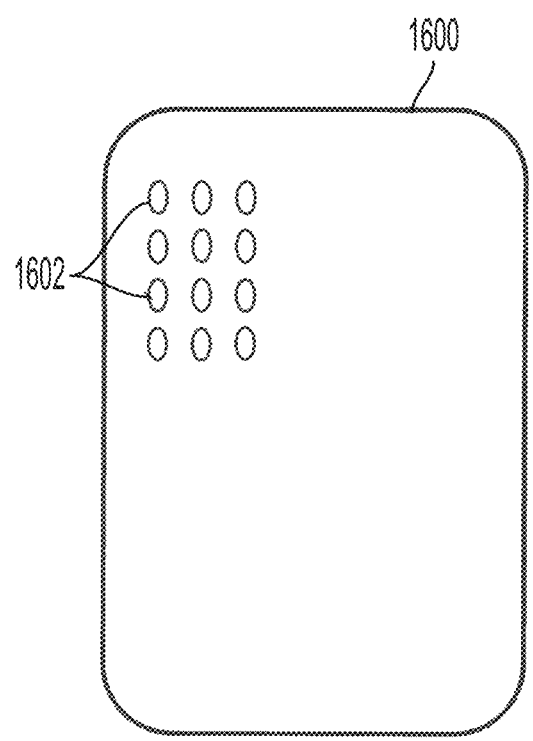
FIG. 16 is a schematic illustration of a nonwoven web defining uniform and homogeneous apertures.

FIG. 16 is a schematic illustration of a nonwoven web 1600 with uniform and homogeneous apertures 1602, on at least a portion thereof. Of course, apertures may be throughout the nonwoven web 1600. The apertures 1602 may be generally the same consistent size and shape (aside from manufacturing tolerances). The apertures may be disposed in the nonwoven web 1600 at generally the same spacing relative to each other (aside from manufacturing tolerances). Nonwoven webs defining uniform and homogeneous apertures as illustrated in FIG. 16 may not be susceptible to the localized high strain that may be encountered during the manufacture of patterned apertured nonwoven webs because the uniform and homogeneous aperture size and spacing may allow for relief from applied stress by rupturing of overbonds at generally the same rate across the entire apertured area of the nonwoven web.

The highly extensible multi-component fiber nonwoven webs of the present disclosure may overcome the problem of fiber breakage under the high strain forces that may be experienced when producing apertured and patterned apertured nonwoven webs. The improved extensibility of the multi-component fiber nonwoven webs of the present disclosure, as measured by the High Speed Tensile Test Method disclosed herein, may allow the nonwoven webs to extend under strain forces exceeding 100% with reduced, significantly reduced, or no fiber breakage. Additionally, the multi-component fiber nonwoven webs of the present disclosure may have an increased fracture point and larger plastic deformation region. When the nonwoven webs are strained beyond the inflection point and into the plastic deformation region, but before the fracture point, the fibers may remain unbroken but permanently deformed. This deformation may allow the apertures to remain open rather than spring back to a pre-strained position.

As mentioned above, the highly extensible nonwoven webs of the present disclosure may comprise a plurality of overbonds. The overbond patterns may be uniform and homogeneous. In other instances, the overbonds may be non-uniform and non-homogeneous. The overbonds may be grouped in arrays of overbonds (see e.g., FIG. 13). The arrays of overbonds may form recognizable shapes, such as hearts and diamonds, for example. The arrays of overbonds may further be grouped into macro-arrays (see e.g., FIG. 14). The overbonds may be ruptured to form apertures.

The highly extensible nonwoven webs of the present disclosure may comprise a plurality of apertures, wherein portions of perimeters of at least some of the apertures comprise a melt lip. The apertures may be patterned apertures. Patterned apertures may allow a nonwoven web to have better depth perception, improved fluid handling properties, and/or a more aesthetically pleasing appearance relative to apertured webs that have homogeneous apertures. The nonwoven webs may have an Effective Open Area of between about 7% and about 30%, between about 10% about 25%, or between about 12% and about 20%, specifically reciting all 0.1% increments within the specified ranges and all ranges formed therein or thereby, according to the Effective Open Area Test described herein. Additionally, the highly extensible nonwoven webs of the present disclosure may define patterned apertures, wherein the maximum measurable aperture area equivalent diameter is between about 1.5 mm and about 10 mm, between about 2 mm and about 8 mm, or between about 3 mm and about 6 mm, specifically reciting all 0.1 mm increments within the specified ranges and all ranges formed therein or thereby, according to the Aperture Area Equivalent Diameter Test disclosed herein.

Methods of Making Apertured and Patterned Apertured Nonwoven Webs

The apertured nonwoven webs and patterned apertured nonwoven webs of the present disclosure may be made generally by using the process generally described in U.S. Pat. No. 5,628,097 entitled "Method for Selectively Aperturing a Nonwoven Web", issued on May 13, 1997, and U.S. Patent Publication No. 2003/0021951, entitled "High Elongation Apertured Nonwoven Web and Method of Making" published Jan. 20, 2003. This process is described in further detail below. The apertured webs or patterned apertured webs may also be made by hydroentanglement, laser cutting, punching with a patterned roll, pin aperturing, or other suitable methods known to those of skill in the art.

Figure 17:
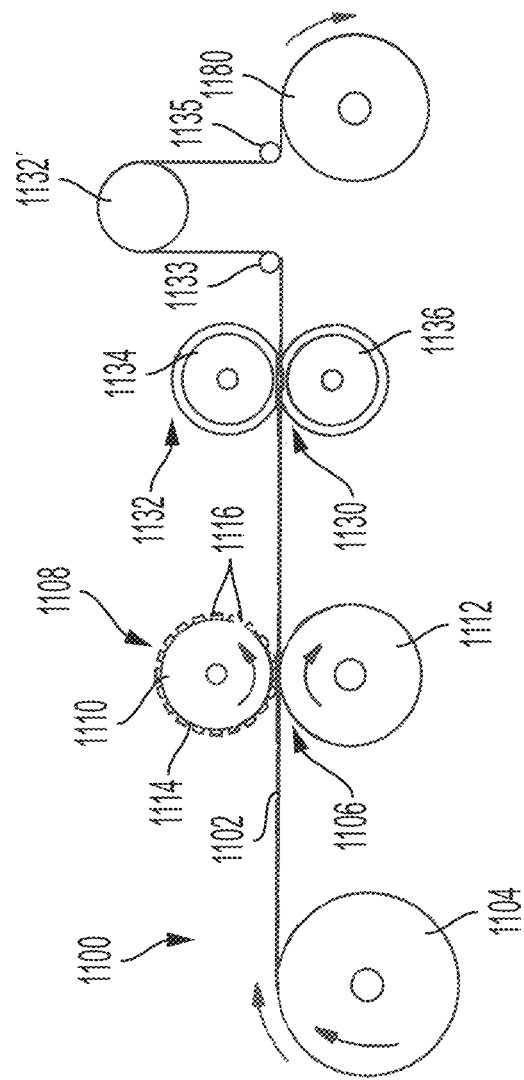
FIG. 17 is a schematic representation of an example process for producing apertured webs or patterned apertured webs.

Referring to FIG. 17, there is schematically illustrated at 1100 one process for forming the apertured webs and/or the patterned apertured webs.

First, a highly extensible nonwoven web 1102 of the present disclosure is supplied as a starting material. The highly extensible nonwoven web 1102 may be supplied as discrete webs, e.g. sheets, patches, etc. of material for batch processing. For commercial processing, however, the highly extensible nonwoven web 1102 may be supplied as roll stock, and, as such it may be considered as having a finite width and an infinite length.

The highly extensible nonwoven web 1102 may be one or more nonwoven materials (same or different). The nonwoven web 1102 may be purchased from a supplier and shipped to where the apertured webs or patterned apertured webs are being formed or the nonwoven web 1102 may be formed at the same location as where the apertured webs or patterned apertured webs are being produced.

The highly extensible nonwoven web 1102 may be unwound from a supply roll 1104 and travel in a direction indicated by the arrow associated therewith as the supply roll 1104 rotates in the direction indicated by the arrow associated therewith. The highly extensible nonwoven web 1102 may pass through a nip 1106 of a weakening roller (or overbonding) arrangement 1108 formed by rollers 1110 and 1112, thereby forming a weakened highly extensible nonwoven web. The weakened highly extensible nonwoven web 1102 comprises a pattern of overbonds, or densified and weakened areas, after passing through the nip 1106. At least some of, or all of, these overbonds are used to form apertures in the highly extensible nonwoven web 1102. Therefore, the overbonds correlate generally to the patterns of apertures created in the highly extensible nonwoven web 1102.

Figure 18:
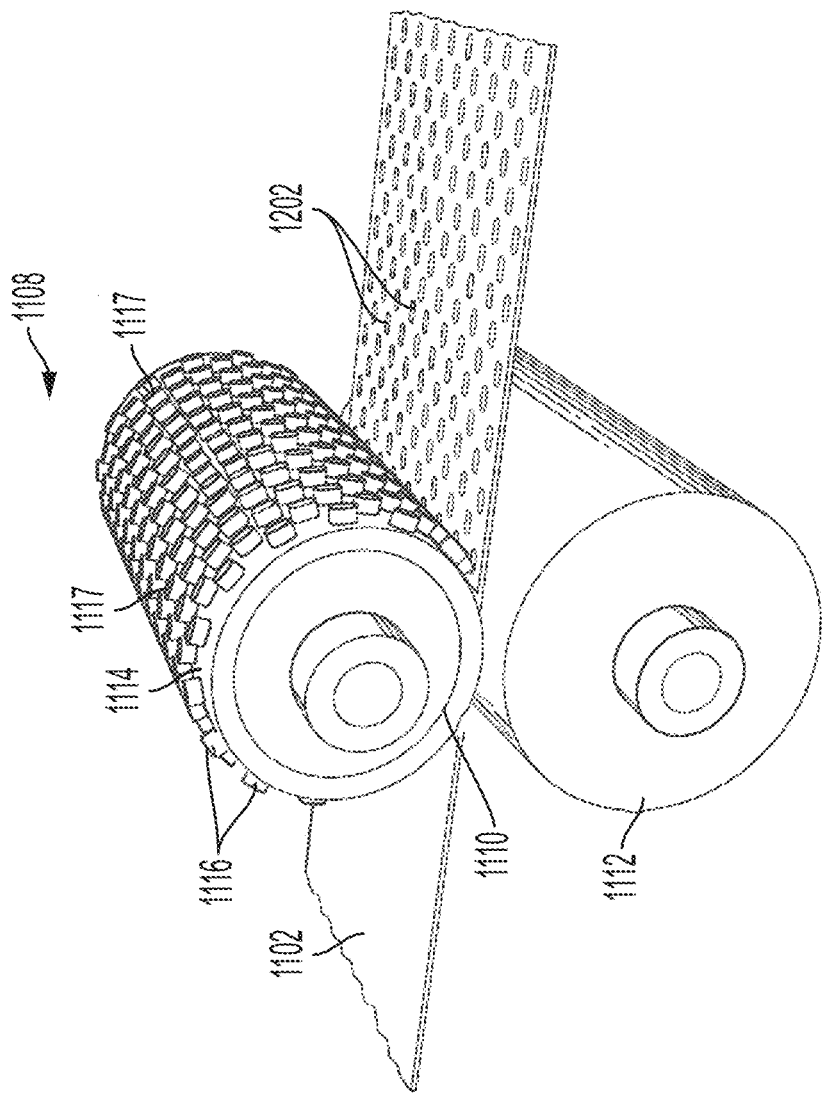
FIG. 18 is a perspective view of a web weakening arrangement of FIG. 17.

Referring to FIG. 18, the highly extensible nonwoven web weakening roller arrangement 1108 may comprises a patterned calendar roller 1110 and a smooth anvil roller 1112. One or both of the patterned calendar roller 1110 and the smooth anvil roller 1112 may be heated and the pressure between the two rollers may be adjusted by known techniques to provide the desired temperature, if any, and pressure to concurrently weaken and melt-stabilize (i.e., overbond) the highly extensible nonwoven web 1102 at a plurality of locations 1202. The temperature of the calendar roller 1110 (or portions thereof) and/or the smooth anvil roller 1112 (or portions thereof) may be ambient temperature or may be in the range of about 100° C. to about 300° C., about 100° C. to about 250° C., about 100° C. to about 200° C., or about 100° C. to about 150° C., specifically reciting all 0.5° C. increments within the specified ranges and all ranges formed therein or thereby. The pressure between the calendar roller 1110 and the smooth anvil roller 1112 may be in the range of about 2,000 pli (pounds per linear inch) to about 10,000 pli, about 3,000 pli to about 8,000 pli, or about 4,500 to about 6,500 pli, specifically reciting all 0.1 pli increments within the specified ranges and all ranges formed therein or thereby. As will be discussed in further detail below, after the highly extensible nonwoven web 1102 passes through the weakening roller arrangement 1108, the highly extensible 1102 may be stretched in the CD, or generally in the CD, by a cross directional tensioning force to at least partially, or fully, rupture the plurality of weakened, melt stabilized locations 1202, thereby creating a plurality of at least partially formed apertures in the highly extensible nonwoven web 1102 coincident with the plurality of weakened, melt stabilized locations 1202.

Figure 19:
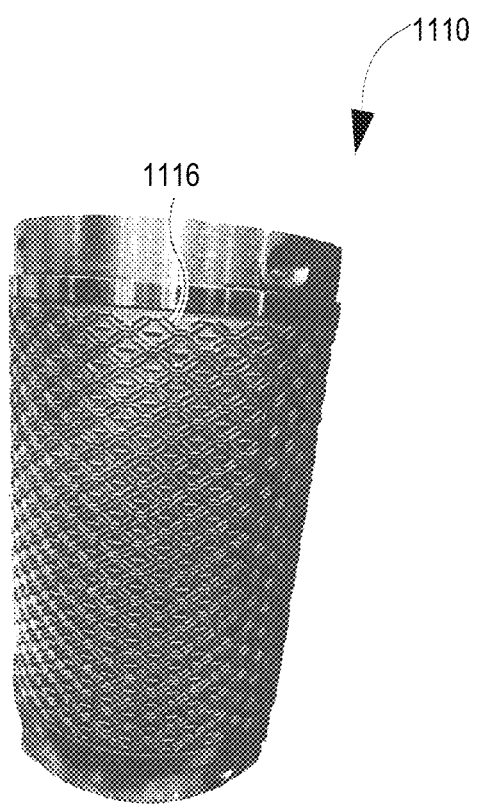
FIG. 19 is a photograph of an example roller that can be used as roller 1110 in the weakening arrangement of FIG. 18, if patterned apertures are desired.

The patterned calendar roller 1110 may be configured to have a cylindrical surface 1114, and a plurality of protuberances or pattern elements 1116 which extend outwardly from the cylindrical surface 1114. The pattern elements 1116 are illustrated as a simplified example of a patterned calendar roller 1110 to produce apertured webs, but more detailed patterned calendar rollers that can be used to produce patterned apertured webs is illustrated in FIG. 19. The protuberances 1116 may be disposed in a predetermined pattern with each of the protuberances 1116 being configured and disposed to precipitate a weakened, melt-stabilized location in the highly extensible nonwoven web 1102 to create a predetermined pattern of weakened, melt-stabilized locations 1202 in the highly extensible nonwoven web 1102. The protuberances 1116 may have a one-to-one correspondence to the pattern of melt stabilized locations in the highly extensible nonwoven web 1102. As shown in FIG. 17, the patterned calendar roller 1110 may have a repeating pattern of the protuberances 1116 which extend about the entire circumference of the surface 1114. Alternatively, the protuberances 1116 may extend around a portion, or portions of the circumference of the surface 1114. Also, a single patterned calendar roller may have a plurality of patterns in various zones (i.e., first zone, first pattern, second zone, second pattern). The protuberances 1116 may have a cross-directional width in the range of about 0.1 mm to about 10 mm, about 0.1 mm to about 5 mm, about 0.1 mm to about 3 mm, about 0.15 mm to about 2 mm, about 0.15 mm to about 1.5 mm, about 0.1 mm to about 1 mm, about 0.1 mm to about 0.5 mm, or about 0.2 to about 0.5 mm, specifically reciting all 0.05 mm increments within the specified ranges and all ranges formed therein or thereby. The protuberances 1116 may have an aspect ratio in the range of about 10:1, about 9:1, about 8:1, about 7:1, about 6:1, about 5:1, about 4:1, about 3:1, about 2:1, about 1.5:1, or about 1.1:1, for example. Other aspect ratios of the protuberances 1116 are also within the scope of the present disclosure. The protuberances 1116, in some forms, may be angled, relative to the machine direction on either side, in the range of about 60 degrees to about 1 degree, about 50 degrees to about 2 degrees, about 45 degrees to about 2 degrees, about 45 degrees to about 5 degrees, about 40 degrees to about 5 degrees, or about 35 degrees to about 5 degrees, specifically reciting all 0.1 degree increments within the specified ranges and all ranges formed therein or thereby. Spacing between adjacent protuberances 1116 in any direction may be greater than about 0.5 mm, greater than about 0.6 mm, greater than about 0.7 mm, greater than about 0.8 mm, greater than about 0.9 mm, greater than about 1 mm, greater than about 1.1 mm, greater than about 1.2 mm, greater than about 1.3 mm, greater than about 1.4 mm, greater than about 1.5 mm, greater than about 2 mm, greater than about 3 mm, or may be in the range of about 0.7 mm to about 20 mm, or about 0.8 to about 15 mm, specifically reciting all 0.1 mm increments within the specified ranges and all ranges formed therein or thereby.

A photograph of an example roller that may be used as patterned calendar roller 1110 in the process 1100 of FIG. 17 to produce the patterned apertured webs of the present disclosure is illustrated in FIG. 19. The pattern of protuberances 1116 on the roller in FIG. 19 are formed in the highly extensible nonwoven web 1102, much like the melt-stabilized locations 1202 of FIG. 18.

The protuberances 1116 may extend radially outwardly from surface 1114 and have distal end surfaces 1117. The anvil roller 1112 may be a smooth surfaced, circular cylinder of steel, rubber or other material. The anvil roller 1112 and the patterned calendar roller 1110 may be switched in position (i.e., anvil on top) and achieve the same result.

From the weakening roller arrangement 1108, the highly extensible nonwoven web 1102 passes through a nip 1130 formed by an incremental stretching system 1132 employing opposed pressure applicators having three-dimensional surfaces which at least to a degree may be complementary to one another.

Figure 20:
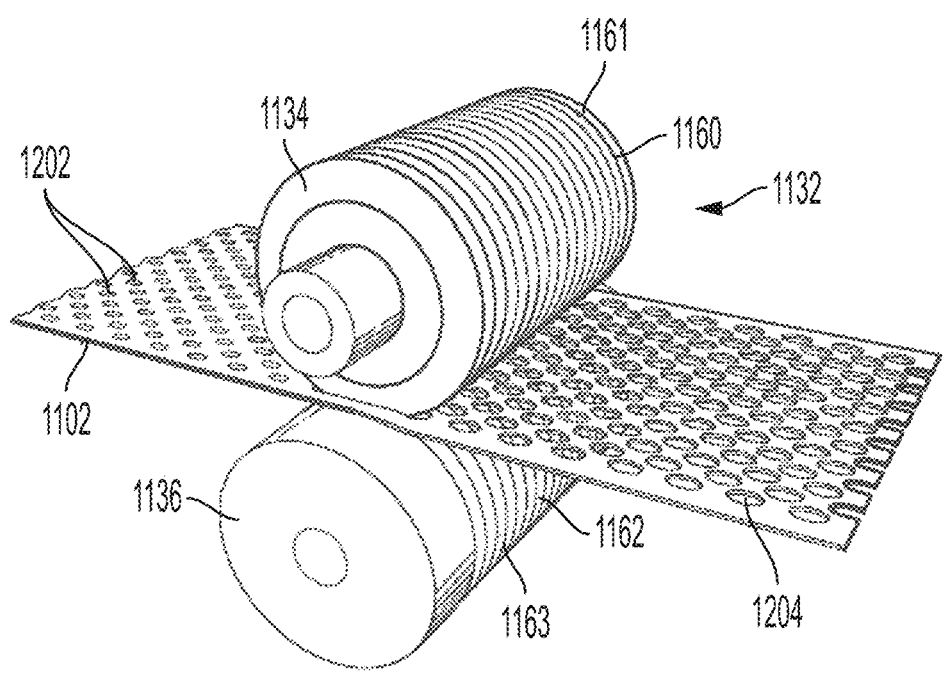
FIG. 20 is a perspective view of an incremental stretching system of FIG. 17.

Referring now to FIG. 20, there is shown a fragmentary enlarged view of the incremental stretching system 1132 comprising two incremental stretching rollers 1134 and 1136. The incremental stretching roller 1134 may comprise a plurality of teeth 1160 and corresponding grooves 1161 which may be present about the entire circumference of roller 1134. The incremental stretching roller 1136 may comprise a plurality of teeth 1162 and a plurality of corresponding grooves 1163. The teeth 1160 on the roller 1134 may intermesh with or engage the grooves 1163 on the roller 1136 while the teeth 1162 on the roller 1136 may intermesh with or engage the grooves 1161 on the roller 1134. The spacing and/or pitch of the teeth 1162 and/or the grooves 1163 may match the pitch and/or spacing of the plurality of weakened, melt stabilized locations 1202 in the highly extensible nonwoven web 1102 or may be smaller or larger. As the highly extensible nonwoven web 1102 having weakened, melt-stabilized locations 1202 passes through the incremental stretching system 1132, the highly extensible nonwoven web 1102 is subjected to tensioning in the CD causing the highly extensible nonwoven web 1102 to be extended (or activated) in the CD, or generally in the CD. Additionally, the highly extensible nonwoven web 1102 may be tensioned in the MD, or generally in the MD. The CD tensioning force placed on the highly extensible nonwoven web 1102 may be adjusted such that it causes the weakened, melt-stabilized locations 1202 to at least partially, or fully, rupture thereby creating a plurality of partially formed, or formed apertures 1204 coincident with the weakened melt-stabilized locations 1202 in the highly extensible nonwoven web 1102. However, the primary bonds of the highly extensible nonwoven web 1102 (in the non-overbonded areas) may be strong enough such that they may not rupture during tensioning, thereby maintaining the highly extensible nonwoven web 1102 in a coherent condition even as the weakened, melt-stabilized locations rupture. However, it may be desirable to have some of the primary bonds rupture during tensioning.

Figure 21:
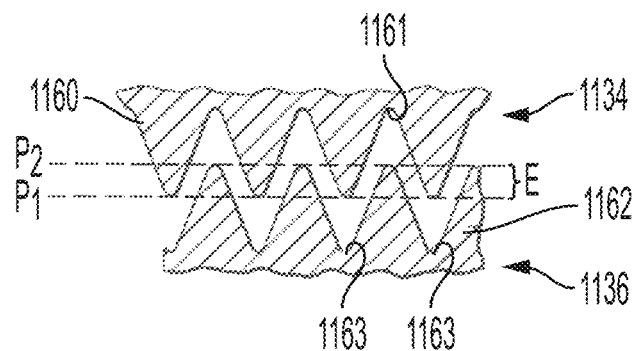
FIG. 21 is an enlarged view showing the details of teeth of the incremental stretching system of FIG. 20.

Referring to FIG. 21, a more detailed view of the teeth 1160 and 1162 and the grooves 1161 and 1163 on the rollers 1134 and 1136 is illustrated. The term "pitch" refers to the distance between the apexes of adjacent teeth. The pitch may be between about 0.02 inches to about 0.30 inches (about 0.51 mm to about 7.62 mm) or may be between about 0.05 inches and about 0.15 inches (about 1.27 mm to about 3.81 mm), specifically reciting all 0.001 inch increments within the above-specified ranges and all ranges formed therein or thereby. The height (or depth) of the teeth may be measured from the base of the tooth to the apex of the tooth, and may or may not be equal for all teeth. The height of the teeth may be between about 0.010 inches (about 0.254 mm) and about 0.90 inches (about 22.9 mm) or may be between about 0.025 inches (about 0.635 mm) and about 0.50 inches (about 12.7 mm), specifically reciting all 0.01 inch increments within the above-specified ranges and all ranges formed therein or thereby. The teeth 1160 in one roll may be offset by about one-half of the pitch from the teeth 1162 in the other roll, such that the teeth of one roll (e.g., teeth 1160) mesh in the valley (e.g., groove 1163) between teeth in the mating roll. The offset permits intermeshing of the two rolls when the rolls are "engaged" or in an intermeshing, operative position relative to one another. The teeth of the respective rolls may only be partially intermeshing in some instances. The degree to which the teeth on the opposing rolls intermesh is referred to herein as the "depth of engagement" or "DOE" of the teeth. The DOE may be constant or not constant. As shown in FIG. 21, the DOE, indicated as "E", is the distance between a position designated by plane P1 where the apexes of the teeth on the respective rolls are in the same plane (0% engagement) to a position designated by plane P2 where the apexes of the teeth of one roll extend inward beyond the plane P1 toward the groove on the opposing roll. The optimum or effective DOE for particular laminate webs may be dependent upon the height and the pitch of the teeth and/or the structure of the material. Some example DOEs may be in the range of about 0.01 inches to about 0.5 inches, about 0.03 inches to about 0.2 inches, about 0.04 inches to about 0.08 inches, about 0.05 inches, or about 0.06 inches, specifically reciting all 0.001 inch increments within the above-specified ranges and all ranges formed therein or thereby.

As the highly extensible nonwoven web 1102 having the weakened, overbonded locations passes through the incremental web stretching apparatus 1132, the nonwoven web 1102 is subjected to tensioning in the cross-machine direction, or substantially in the cross-machine direction, thereby causing the nonwoven web 1102 to be extended in the cross-machine direction. The tensioning force placed on the nonwoven web 1102 may be adjusted by varying the pitch, DOE, or teeth size, such that the incremental stretching is sufficient to cause the weakened, overbonded locations 1202 to at least partially, or fully rupture, thereby creating, or at least partially creating, a plurality of apertures 1204 coincident with the weakened, overbonded locations in the nonwoven web 1102. The highly extensible nonwoven webs of the present disclosure may exhibit improved extensibility in the cross-machine direction to accommodate the tensioning force used to rupture overbonded areas. The improved extensibility may allow for the fibers of the nonwoven web to remain intact in non-overbonded areas, resulting in a stronger web which may produce less lint.

Referring to FIG. 17, after the highly extensible nonwoven web 1102 passes through the incremental web stretching apparatus 1132, the nonwoven web 1102 may be advanced to and at least partially around a cross-machine directional tensioning apparatus 1132'. The cross-machine directional tensioning apparatus 1132' may be offset from the main processing line by running the web partially around two idlers 1133 and 1135 or stationary bars, for example. In other instances, the cross-machine tensioning apparatus 1132' may be positioned in line with the main processing line. The cross-machine directional tensioning apparatus 1132' may comprise a roll that comprises at least one outer longitudinal portion that expands along a longitudinal axis of the roll, relative to a middle portion of the roll, to stretch and/or expand the nonwoven web 1102 in the cross-machine direction. Instead of or in addition to expanding along the longitudinal axis of the roll, the outer longitudinal portion may be angled relative to the longitudinal axis of the roll in a direction away from the nonwoven web 1102 being advanced over the roll to stretch the nonwoven web 1102 in the cross-machine direction or generally in the cross-machine direction. In an instance, the roll may comprise two outer longitudinal portions that each may expand in opposite directions generally along the longitudinal axis of the roll. The two outer portions may both be angled downwards in a direction away from the nonwoven web 1102 being advanced over the roll. This movement or positioning of the outer longitudinal portions of the roll allows for generally cross-machine directional tensioning of the nonwoven web1102, which may cause the plurality of overbonds 1202 to rupture and/or be further defined or formed into apertures 1204.

The outer longitudinal portions of the roll may comprise vacuum, a low tack adhesive, a high coefficient of friction material or surface, such as rubber, and/or other mechanisms and/or materials to hold the highly extensible nonwoven web 1102 to the outer lateral portions of the roll during movement of the outer longitudinal portion or portions relative to the middle portion of the roll. The vacuum, low tack adhesive, high coefficient of friction material or surface, and/or other mechanisms and/or materials may prevent, or at least inhibit, the held portions of the highly extensible nonwoven web 1102 from slipping relative to the longitudinal axis, A, of the roll during stretching of the outer lateral portions of the material in the cross-machine direction or generally in the cross-machine direction.

Figure 22:
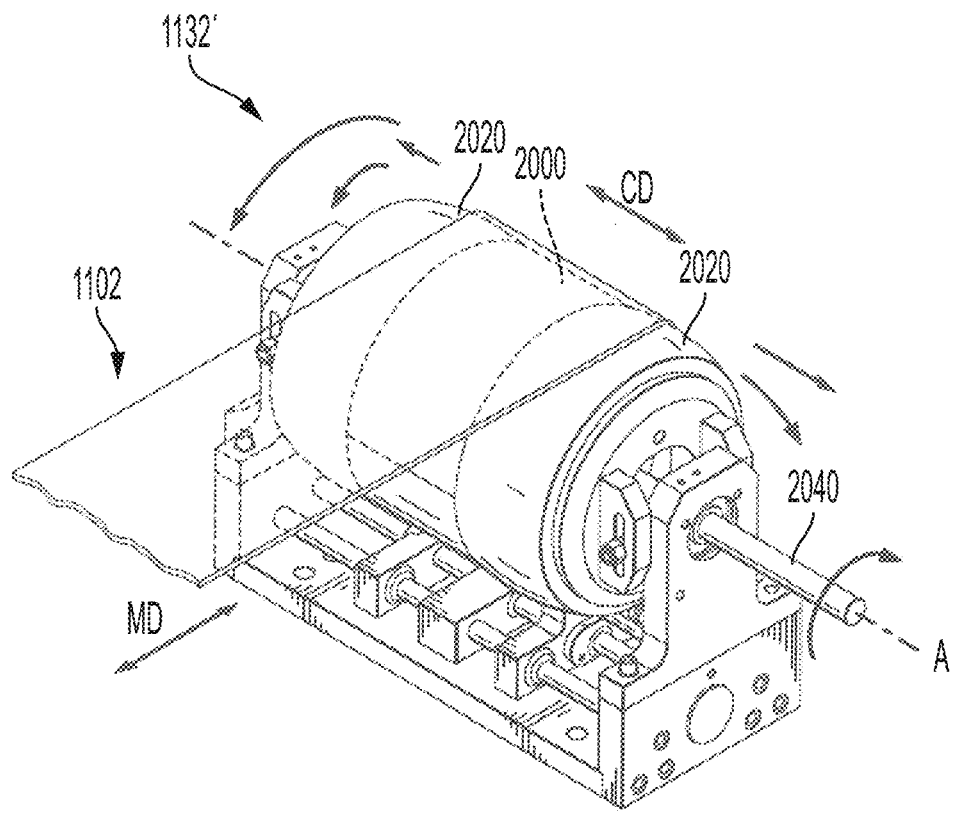
FIG. 22 is a perspective view of an example cross-machine directional tensioning apparatus of FIG. 17.

FIG. 22 is a top perspective view of the example cross-machine directional tensioning apparatus 1132'. The cross-machine directional tensioning apparatus 1132' may comprise a roll comprising a middle portion 2000 and two outer longitudinal portions 2020 situated on either end of the middle portion 2000. The roll may rotate about its longitudinal axis, A, on a drive shaft 2040. The roll may rotate relative to the drive shaft 2040 or in unison with the drive shaft 2040, as will be recognized by those of skill in the art. The highly extensible nonwoven web 1102 may be advanced over the entire cross-machine directional width of the middle portion 2000 and at least portions of the cross-machine directional widths of the outer longitudinal portions 2020. The highly extensible nonwoven web 1102 may be advanced over at least about 5% up to about 80% of the circumference of the roll so that the cross-machine directional stretching may be performed.

Figure 23:
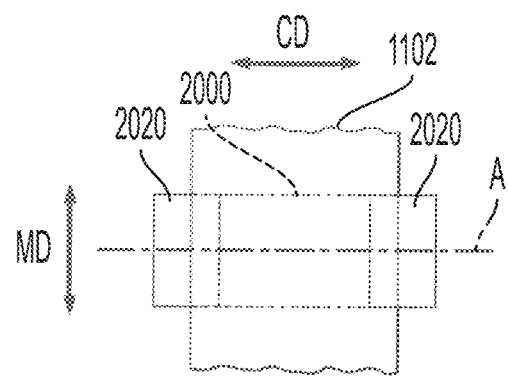
FIG. 23 is a schematic representation of a front view of an example cross-machine directional tensioning apparatus with outer longitudinal portions in an unexpanded and non-angled position relative to a middle portion.
Figure 24:
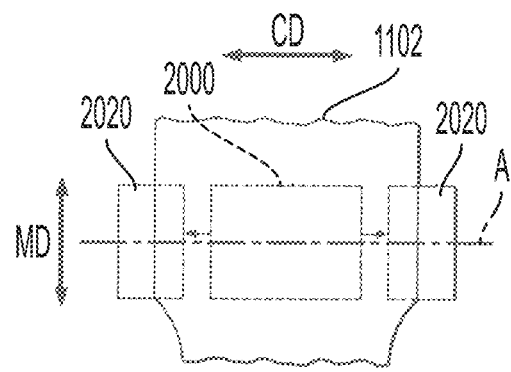
FIG. 24 is a schematic representation of a front view of the cross-machine directional tensioning apparatus of FIG. 23 with the outer longitudinal portions in a longitudinally expanded position relative to the middle portion in accordance with the present disclosure.
Figure 25:
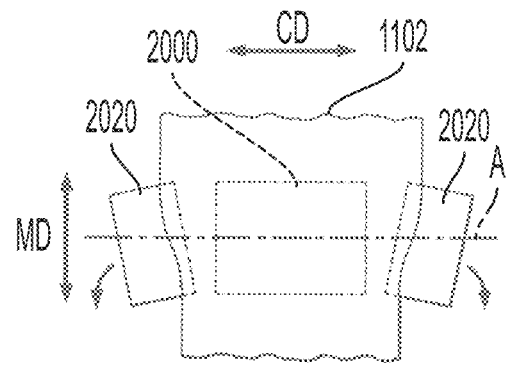
FIG. 25 is a schematic representation of a front view of the cross-machine directional tensioning apparatus of FIG. 23 with the outer longitudinal portions in an angled and expanded position relative to the middle portion.
Figure 26:
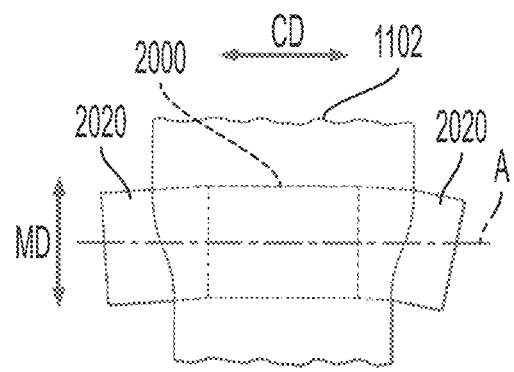
FIG. 26 is a schematic representation of a front view of a cross-machine directional tensioning apparatus with outer longitudinal portions fixed in an angled position relative to a middle portion.

FIG. 23 is a schematic representation of a front view of an example cross-machine directional tensioning apparatus with outer longitudinal portions 2020 in an unexpanded or non-angled position relative to the middle portion 2000. FIG. 24 is a schematic representation of a front view of the cross-machine directional tensioning apparatus of FIG. 23 with the outer longitudinal portions 2020 in a longitudinally expanded position relative to the middle portion 2000. FIG. 25 is a schematic representation of a front view of the cross-machine directional tensioning apparatus of FIG. 23 with the outer longitudinal portions 2020 in an angled and expanded position relative to the middle portion 2000. Regarding FIG. 25, the outer longitudinal portions 2020 may merely move or slide in a direction generally perpendicular to the machine direction of the highly extensible nonwoven web 1102 passing over the roll to apply the cross-machine directional tensioning force to the highly extensible nonwoven web 1102. FIG. 26 is a schematic representation of a front view of a cross-machine directional tensioning apparatus with the outer longitudinal portions 2020 fixed in an angled position relative to the middle portion 2000 to apply the cross-machine directional tensioning force to the highly extensible nonwoven web 1102. In such a form, the middle portion 2000 and each of the outer longitudinal portions 2020 may comprise a separate roll.

Regardless of whether one or both of the outer longitudinal portions 2020 is moved, slid, rotated, fixed, and/or expanded relative to the middle portion 2000, this relative motion or positioning between the outer longitudinal portions 2020 and the middle portion 2000 stretches the highly extensible nonwoven web 1102 in a cross-machine direction to further rupture or further define the weakened locations 1202 in the highly extensible nonwoven web 1102 and create, or further form, a plurality the apertures 2040 in the highly extensible nonwoven web 1102. In an instance, the cross-machine directional tensioning apparatus may be similar to, or the same as, the incremental stretching apparatus 1132 to apply the cross-machine directional tensioning force. In still other instances, any suitable cross-machine directional tensioning apparatus may be used to apply the cross-machine directional tensioning force to the highly extensible nonwoven web 1102.

If desired, the incremental stretching step or the cross-machine directional stretching step described herein may be performed at elevated temperatures. For example, the highly extensible nonwoven web 1102 and/or the rolls may be heated. Utilizing heat in the stretching step may serve to soften the highly extensible nonwoven web, and may aid in extending the fibers without breaking.

Referring again to FIG. 17, the highly extensible nonwoven web 1102 may be taken up on wind-up roll 1180 and stored. Alternatively, the highly extensible nonwoven web 1102 may be fed directly to a production line where it is used to form a portion of an absorbent article or other consumer product.

It is important to note that the overbonding step illustrated in FIGS. 17 and 18 could be performed by the material supplier and then the highly extensible nonwoven web may be shipped to a consumer product manufacturer to perform step 1132. In fact, the overbonding step may be used in the nonwoven production process to form overbonds, which may be in addition to, or in lieu of, primary bonds formed in the nonwoven production process. Alternatively, the material supplier may fully perform the steps illustrated in FIG. 17 and then the highly extensible nonwoven web may be shipped to the consumer product manufacturer. The consumer product manufacturer may also perform all of the steps in FIG. 17 after obtaining a nonwoven material from a nonwoven material manufacturer.

One of ordinary skill in the art will recognize that it may be advantageous to submit the highly extensible nonwoven web 1102 to multiple incremental stretching processes depending on various desired characteristics of the finished product. Both the first and any additional incremental stretching may either be done on-line or off-line. Furthermore, one of ordinary skill will recognize that the incremental stretching may be done either over the entire area of the highly extensible nonwoven web or only in certain regions of the highly extensible nonwoven web depending on the final desired characteristics.

EXAMPLES

Comparative Example 1

The continuous fiber nonwoven web described herein as Comparative Example 1 is a2-layer face to face contact nonwoven web, each layer being a 25 gsm core/sheath bi-component spunbond nonwoven with 50% European sourced polypropylene 7e (core) and 50% European sourced polyethylene 7e (sheath) having an initial material width of 105 mm. Fiber attenuation is minimized to achieve high extensibility while still maintaining standard commercial throughput. The nonwoven web is point bonded with 18% (bond area) standard oval pattern and optimized to prevent, or at least inhibit, linting. The nonwoven web is subsequently overbonded and the overbonds are ruptured to form patterned apertures as illustrated generally in FIG. 14.

Comparative Example 2

The continuous fiber nonwoven web described herein as Comparative Example 2 is a25 gsm core/sheath bi-component spunbond nonwoven with 50% European sourced polypropylene 7e (core) and 50% European sourced polyethylene 7e (sheath) having an initial material width of 105 mm. Fiber attenuation is minimized to achieve high extensibility while still maintaining standard commercial throughput. The nonwoven web is point bonded with 18% standard oval pattern and optimized to prevent, or at least inhibit, linting.

Comparative Example 3

The continuous fiber nonwoven web described herein as Comparative Example 3 is a25 gsm core/sheath bi-component spunbond nonwoven with 50% European sourced polypropylene 7e (core) and 50% polyethylene 00w (sheath) having an initial material width of 105 mm. Fiber attenuation is minimized to achieve high extensibility while still maintaining standard commercial throughput. The nonwoven web is point bonded with 18% standard oval pattern and optimized to prevent, or at least inhibit, linting.

Example 1

The highly extensible continuous fiber nonwoven web described herein as Example 1 is a 2-layer face to face contact nonwoven web, each layer being a 25 gsm core/sheath bi-component spunbond nonwoven with 50% European sourced polypropylene 7e (core) and 50% European sourced polyethylene 10e (sheath) having an initial material width of 105 mm. Fiber attenuation is minimized to achieve high extensibility while still maintaining standard commercial throughput. The nonwoven web is point bonded with 18% standard oval pattern and optimized to prevent, or at least inhibit, linting. The nonwoven web is subsequently overbonded and the overbonds are ruptured to form patterned apertures as generally illustrated in FIG. 14.

Example 2

The highly extensible continuous fiber nonwoven web described herein as Example 2 is a 2-layer face to face contact nonwoven web, each layer being a 25 gsm core/sheath bi-component spunbond nonwoven with 50% European sourced polypropylene 10e (core) and 50% European sourced polyethylene 10e (sheath) having an initial material width of 105 mm. Fiber attenuation is minimized to achieve high extensibility while still maintaining standard commercial throughput. The nonwoven web is point bonded with 18% standard oval pattern and optimized to prevent, or at least inhibit, linting. The nonwoven web is subsequently overbonded and the overbonds are ruptured to form patterned apertures as generally illustrated in FIG. 14.

Example 3

The highly extensible continuous fiber nonwoven web described herein as Example 3 is a 2-layer face to face contact nonwoven web, each layer being a 25 gsm core/sheath bi-component spunbond nonwoven with 50% European sourced polypropylene 99e (core) and 50% European sourced polyethylene 10e (sheath) having an initial material width of 105 mm. Fiber attenuation is minimized to achieve high extensibility while still maintaining standard commercial throughput. The nonwoven web is point bonded with 18% standard oval pattern and optimized to prevent, or at least inhibit, linting. The nonwoven web is subsequently overbonded and the overbonds are ruptured to form patterned apertures as generally illustrated in FIG. 14.

Example 4

The highly extensible continuous fiber nonwoven web described herein as Example 4 is a 2-layer face to face contact nonwoven web, each layer being a 25 gsm core/sheath bi-component spunbond nonwoven with 50% European sourced polypropylene 99e (core) and 50% European sourced polyethylene 10e (sheath) having an initial material width of 105 mm. Fiber attenuation is minimized to achieve high extensibility while still maintaining standard commercial throughput. The nonwoven web is point bonded with 18% standard oval pattern and optimized to prevent, or at least inhibit, linting. The point bonding is performed at a temperature 5° C. less than the Example 3. The nonwoven web is subsequently overbonded and the overbonds are ruptured to form patterned apertures as generally illustrated in FIG. 14.

Example 5

The highly extensible continuous fiber nonwoven web described herein as Example 4 is a 25 gsm core/sheath bi-component spunbond nonwoven with 50% North America sourced polypropylene 99*a* (core) and 50% polyethylene 00w (sheath) having an initial material width of 105 mm. Fiber attenuation is minimized to achieve high extensibility while still maintaining standard commercial throughput. The nonwoven web is point bonded with 18% standard oval pattern and optimized to prevent, or at least inhibit, linting.

Example 6

The highly extensible continuous fiber nonwoven web described herein as Example 6 is a 25 gsm core/sheath bi-component spunbond nonwoven with 50% North America sourced polypropylene 99*a* (core) and 50% North America Sourced polyethylene 10a (sheath) having an initial material width of 105 mm. Fiber attenuation is minimized to achieve high extensibility while still maintaining standard commercial throughput. The nonwoven web is point bonded with 18% standard oval pattern and optimized to prevent, or at least inhibit, linting.

TABLE 1

Apertured Nonwoven Web Examples

| Variable ID | Core/Sheath, Point Bonding Conditions | PP Crystallinity (%) | PP Melting Temp. (° C.) | PE Speed of Crystallization (ms) | Extensibility (%) |
| --- | --- | --- | --- | --- | --- |
| Comparative Example 1 | PP7e/PE7e, Standard | 42.6 | 160.8 | 1362 | 266 |
| Example 1 | PP7e/PE10e, Standard | 40.0 | 160 | 1349 | 347 |
| Example 2 | PP10e/PE10e, Standard | 40.5 | 161.2 | 1349 | 336 |
| Example 3 | PP99e/PE10e, Standard | 30 | 150.9 | 1349 | 376 |
| Example 4 | PP99e/PE10e, Low (-5° C.) | 30 | 150.9 | 1349 | 422 |

TABLE 2

Apertured Nonwoven Web Examples (cont.)

| Variable ID | Neckdown Modulus (N/m) | MD Material Elongation (%) | Effective Open Area (%) | Tape Stripping (%) | Peel Strength (N) | Final Width (mm) |
| --- | --- | --- | --- | --- | --- | --- |
| Comparative Example 1 | 1400 | 2.7 | 10.6 | 12.20 | 0.74 | 176 |
| Example 1 | 1683 | 2.2 | 10.5 | 7.10 | 0.82 | 176 |
| Example 2 | 1441 | 2.6 | 11.7 | 7.80 | 0.84 | 183 |
| Example 3 | 1720 | 2.3 | 12.4 | 4.80 | 0.92 | 190 |
| Example 4 | 1309 | 2.2 | 12.6 | 5.80 | 0.95 | 183 |

TABLE 3

Nonwoven Web Examples

| Variable ID | Core/Sheath | PP Crystallinity (%) | PP Melting Temp. (° C.) | PE Speed of Crystallization (ms) | Extensibility (%) | Material Elongation (%) |
| --- | --- | --- | --- | --- | --- | --- |
| Comp. Example 2 | PP7e/PE7e | 42.6 | 160.8 | 1362 | 266 | 2.7 |
| Comp. Example 3 | PP7e/PE00w | 42.5 | 160 | 1368 | 269 | 2.6 |
| Example 5 | PP99a/PE00w | 28.5 | 151.4 | 1368 | 364 | 3.7 |
| Example 6 | PP99a/PE10a | 29.0 | 150.2 | 1349 | 404 | 2.6 |

Examples 1, 2, 3, 4, and Comparative Example 1 were tested for Polypropylene (PP) Fiber Crystallinity, Polyethylene (PE) Resin Speed of Crystallization, nonwoven web strength as tested by Neckdown Modulus at 0-3% and MD (machine direction) Material Elongation, Extensibility, Effective Open Area, Tape Stripping, and Peel Strength, according to test methods presented herein. The data from these testes are presented in Tables 1 and 2. Referring to Table 1, the highly extensible nonwoven webs of the present disclosure in Examples 1, 2, 3, and 4 have greater extensibility under high speed tensile test, indicating greater extensibility, as compared to the Comparative Example 1. The data suggest that lower PP Crystallinity results are generally associated with higher Extensibility results. Furthermore, comparing Comparative Example 1 versus Example 1, lower PE Speed of Crystallization in the sheath PE component may further reduce PP Crystallinity of the core component. Without wishing to be bound by theory, it is believed that a faster crystallizing sheath component may protect the core component, leading to a more amorphous core component as demonstrated by a reduction in Crystallinity.

Table 2 presents data on Neckdown Modulus, MD Material Elongation, Effective Open Area, Tape Stripping, Peel Strength, and Final Width. Examples 1, 2, 3, and 4 maintain acceptable Neckdown Modulus scores (greater than about 1300 N/m), which is indicative of enough strength to resist narrowing in the cross-machine direction when exposed to machine-direction stress. Additionally, Examples 1, 2, 3, and 4 show improved Tape Stripping scores as compared to Comparative Example 1, which indicates the amount of lint produced by a nonwoven web after value added features are created. Without wishing to be bound by theory, it is believed that the increased extensibility of Examples 1, 2, 3, and 4 results in less fiber breakage during production and/or during cross-machine directional overbonding/rupturing process, as described herein. Fiber breakage is believed to result in lint production by broken fibers coming loose from the web structure. With the improved extensibility shown in Examples 1, 2, 3, and 4, it is believed that rupturing takes place in the plastic deformation region of the stress-strain curve, resulting in a larger effective open area and a wider final aperture width. As two nonwoven webs were joined by a point bonding process to form a laminate prior to the high strain overbonding/rupturing process that formed apertures in these examples, the peel strength required to separate the final nonwoven web also increases as there may have been less damage to melt lips surrounding the apertures, thus strengthening the laminates.

Final width was measured on relaxed nonwoven web examples from edge to edge along the cross-direction after patterned apertures were formed. MD Material Elongation refers to material elongation in the machine direction when force applied in the same direction reaches 5 Newtons for every 1 centimeter of sample in the cross-direction, according to WSP 110.4-2005 (where the test sample width is 50 mm, jaw distance is 100 mm, speed is 100 mm/min, and preload is 0.1N). This represents elongation of the nonwoven web at the low-strain portion of the tensile curve. MD Material Elongation scores of Examples 1-4 were comparable to Comparative Example 1.

Table 3 presents data from Comparative Examples 2 and 3 and Examples 5 and 6, which are non-apertured nonwoven webs. Data from non-apertured nonwoven webs also shows that reduced PP Crystallinity is associated with increased nonwoven web extensibility. The addition of a faster crystalizing PE in Example 6 further increased the extensibility. Also, the increased extensibility did not negatively impact the MD Material Elongation scores, as the scores remained comparable among the examples.

Test Procedures

Enthalpies of Fusion and Crystallinity Test

The Enthalpies of Fusion and Crystallinity Test is used to determine the Enthalpy of Fusion and Percent Crystallinity parameters. The Enthalpies of Fusion and Crystallinity Test includes performing ASTM E793-06 with the following additional guidance. A specimen from a nonwoven web is die-cut from a sample nonwoven web. The mass of the specimen is 3±2 mg, and the mass of the specimen is recorded to the nearest 0.01 mg. (If multiple layers are required to achieve the requisite sample mass, the sample nonwoven web is folded such that multiple layers of the same nonwoven web are punched simultaneously to produce the specimen.) Dry nitrogen is used as the purge gas in a Differential Scanning calorimeter (DSC). The range of testing temperature is from −90° C. to 200° C. The rate of increase temperature in DSC is 20° C./min, and the rate of decrease temperature is 20° C./min. The melting peak temperature is determined as described § 11 of ASTM E793-06. The mass-normalized enthalpy of fusion is calculated as specified in § 11 in ASTM E793-06 and reported as the Enthalpy of Fusion Parameter ($\Delta H_m$) in unit of Joules per gram (J/g) to the nearest 0.01 J/g.

From the Enthalpy of Fusion Parameter, the Percent Crystallinity is determined using the following equation $$\text{Percent Crystallinity } [\%] = \frac{\Delta H_m}{\Delta H_m^\circ \times W} \times 100\%$$

where $\Delta H_m$ is the mass-normalized Enthalpy of Fusion Parameter, $\Delta H°_m$ is the mass-normalized Enthalpy of Fusion of 100% crystalline polypropylene (taken here to be 207 J/g), and W is the weight fraction of polypropylene.

Percent Crystallinity is reported to the nearest integer value in percentage.

Primary Bond Area Test

The Primary Bond Area Test is used to determine the primary bond area percentage of a nonwoven web. Identify a single repeat pattern of bond shapes and areas between them, and enlarge the image such that the repeat pattern fills the field of view. In ImageJ, draw a rectangle that circumscribes the repeat pattern. Calculate the area of the rectangle and record to the nearest 0.001 mm². Next, with the area tool, trace the individual bond shapes, or portions thereof, that are entirely within the repeat pattern/rectangle. Calculate the area of each individual bond shape and add the areas of all bond shapes or portions thereof that are within the repeat pattern/rectangle. Record to the nearest 0.001 mm². Calculate as follows:

Bond Area %=(Sum of areas of bond shapes within repeat pattern)/(total area of repeat pattern)× 100%

Repeat for a total of three non-adjacent regions randomly selected across the sample. Record as Percent Bond Area to the nearest 0.01%. Calculate the average and standard deviation of all 18 of the bond area percentage measurements and report to the nearest 0.01%.

Effective Open Area Test and Aperture Area Equivalent Diameter Test

The percent effective open area and the aperture area equivalent diameter are obtained from aperture specimen images acquired using a flatbed scanner. The scanner is capable of scanning in reflectance mode at a resolution of 6400 dpi and 8 bit grayscale (a suitable scanner is an Epson Perfection V750 Pro from Epson America Inc., Long Beach CA, or equivalent). The scanner is interfaced with a computer running an image analysis program (a suitable program is ImageJ v. 1.47, National Institute of Health, USA, or equivalent). The specimen images are distance calibrated against an acquired image of a ruler certified by NIST. The aperture specimen is backed with a black glass tile (P/N 11-0050-30, available from HunterLab, Reston, VA, or equivalent) prior to acquiring the image. The resulting grayscale image is then converted to a binary image via a threshold gray-level value, enabling the separation of open aperture regions from specimen material regions, and these regions analyzed using the image analysis program. All testing is performed in a conditioned room maintained at about 23±2° C. and about 50±2% relative humidity.

Sample Preparation:

To obtain a specimen, the absorbent article or other product is taped to a rigid flat surface in a planar configuration. Any leg elastics present may be cut to facilitate laying the article flat. The outer boundary of the region lying above the absorbent core of the article is identified and marked on the apertured layer. The specimen of apertured layer is removed from the underlying layers of the article by cutting around the outer perimeter of the article with a razor blade. The apertured layer specimen is carefully removed such that its longitudinal and lateral extension is maintained to avoid distortion of the apertures. A cryogenic spray (such as Cyto-Freeze, Control Company, Houston TX, or equivalent) can be used to remove the specimen from the underlying layers if necessary. Five replicate specimens obtained from five substantially similar articles are prepared for analysis. An apertured substrate raw material is prepared for testing by extending or activating it under the same process conditions, and to the same extent, as it would be for use on the absorbent article. The samples are conditioned at about 23° C.±2 C.° and about 50%±2% relative humidity for 2 hours prior to testing.

Image acquisition:

The ruler is placed on the scanner bed such that it is oriented parallel to the sides of the scanner glass. An image of the ruler (the calibration image) is acquired in reflectance mode at a resolution of 6400 dpi (approximately 252 pixels per mm) and in 8-bit grayscale. The calibration image is saved as an uncompressed TIFF format file. After obtaining the calibration image, the ruler is removed from the scanner glass and all specimens are scanned under the same scanning conditions. An apertured specimen is placed onto the center of the scanner bed, lying flat, with the outward facing surface of the specimen facing the scanner's glass surface. The corners and edges of the specimen are secured such that its original longitudinal and lateral extension, as on the article prior to removal, is restored. The specimen is oriented such that the machine direction (MD) and cross direction (CD) of the apertured specimen layer are aligned parallel with and perpendicular to the sides of the scanner's glass surface and that the resulting specimen image has the MD vertically running from top to bottom. The black glass tile is placed on top of the specimen, the scanner lid is closed, and a scanned image of the entire specimen is acquired. The specimen image is saved as an uncompressed TIFF format file. The remaining four replicate specimens are scanned and saved in like fashion. Prior to analysis, all specimen images are cropped to the largest rectangular field of view contained within the apertured region which had been located above the absorbent core of the article.

Percent Effective Open Area and Aperture Area Equivalent Diameter Calculations:

The calibration image file is opened in the image analysis program and a linear distance calibration is performed using the imaged ruler. This distance calibration scale is applied to all subsequent specimen images prior to analysis. A specimen image is in the image analysis program and the distance scale is set using the distance calibration. The 8-bit grayscale image is then converted to a binary image (with "zero" or "black" corresponding to the aperture regions) in the following way: If the histogram of gray level (GL) values (ranging from 0 to 255, one bin with propensity $P_i$ per gray level i) has exactly two local maxima, the threshold gray level value t is defined as that value for which $P_{t-1} > P_t$ and $P_t \leq P_{t+i}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-1} > P_t$ and $P_t \leq P_{t+1}$. This procedure identifies the gray level (GL) value for the minimum population located between the dark pixel peak of the aperture holes and the lighter pixel peak of the specimen material. If the histogram contains either zero or one local maximum, the method cannot proceed further, and no output parameters are defined.

Each of the discrete aperture regions is analyzed using the image analysis program. All individual aperture areas are measured and recorded to the nearest 0.01 $mm^2$, including partial apertures along the edges of the image. Concurrently, the equivalent diameter of each aperture area is calculated from the measured area and recorded to the nearest 0.1 mm. Any apertures with an area less than 0.3 $mm^2$ are defined as "non-effective" and discarded. The remaining apertures, so-called "effective" aperture areas that include whole and partial apertures, are summed in area. This sum is then divided by the total area included in the image. This value is multiplied by 100% and reported as the effective open area to the nearest 0.01%. The arithmetic mean of the equivalent diameters among all "effective" apertures is calculated and recorded as the aperture area equivalent diameter of the specimen.

The remaining four specimen images are analyzed similarly. The arithmetic mean percent effective area values for the five replicate specimens is calculated and reported to the nearest 0.01%. Similarly, the arithmetic mean of the aperture area equivalent diameter values for the five replicate specimens is calculated and reported to the nearest 0.1 mm.

High Speed Tensile Test

The High Speed Tensile Test is used to measure the Tensile Strength of a material sample at a relatively high strain rate. The method uses a suitable tensile tester such as an MTS 810, available from MTS Systems Corp., Eden Prairie, Minnesota, or equivalent, equipped with a servo-hydraulic actuator capable of facilitating speeds exceeding 1 m/s after 5 mm of crosshead displacement, and at least approximately 1.5 m/s after 10 mm of crosshead displacement. The tensile tester is fitted with a 50-lb force transducer (part 9712 B50 from Kistler North America, Amherst, New York, or equivalent), and a signal conditioner with a dual mode amplifier (part 5010 from Kistler North America, or equivalent).

Figure 27:
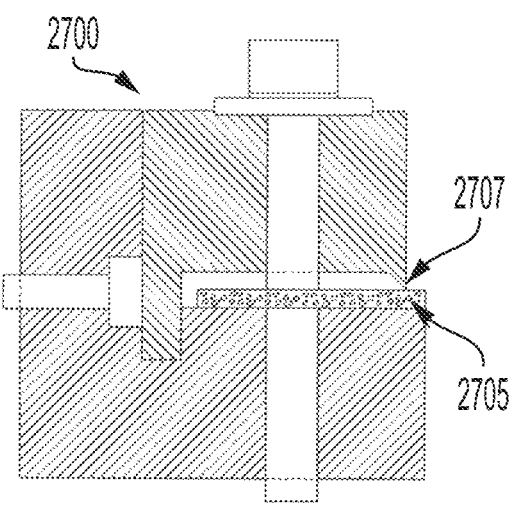
FIG. 27 is a cross-section view of a line contact grip used for the High Speed Tensile Test herein.
Figure 28:
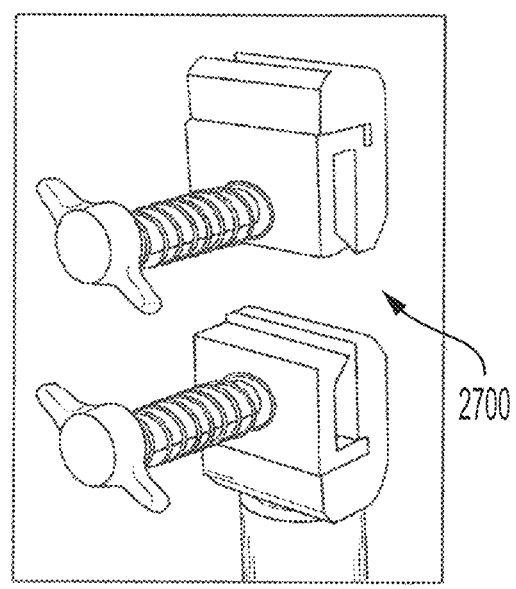
FIG. 28 is a perspective view of a pair of opposing line contact grips for use in the High Speed Tensile Test herein.

FIG. 27 is a cross-sectional view of a single line contact grip 2700 used in this test. The line grip 2700 is selected to provide a well-defined gauge and avoid undue slippage of the specimen. The specimen is positioned such that it has minimal slack. The apex 2707 of the grip 2700 is ground to give good gauge definition while avoiding damage or cutting of the specimen. A portion of the grip 2700 may be configured to include a material 2705 that reduces the tendency of a specimen to slip. FIG. 28 illustrates a pair of opposing line contact grips 2700 suitable for use in this test. A pair of grips of varying specific design but with equivalent function (i.e. capable of facilitating a well-defined 3-mm gauge length, no undue slippage, and at least as wide as the specimens analyzed) to those described above may be used alternatively.

For a nonwoven sample of interest, five like specimens having dimensions of 50.8 mm wide by 15 mm long are cut. The short dimension of each specimen is parallel to the machine direction of the nonwoven. If the specimens are extracted from finished absorbent article(s), the short dimension of the specimen is oriented parallel to the longitudinal axis of the absorbent article. The line contact grips are moved to a grip separation of 3.0 millimeters (i.e. the distance between the lines of contact between specimen and grip surface). The specimen is mounted in the line contact grips, and a thin piece of tape to help hold the specimen straight and flat while mounting in grips. (If used, tape must remain behind the lines of gripping so that it does not interfere with the specimen gauge during the test.) The line contact grips are moved closer together to put as much slack as possible into the film specimen without the line contact grips interfering with one another. Actuator movement is selected such that the specimen experiences relative grip speed of approximately 1 m/s at an engineering strain of 1 and 1.5 m/s at an engineering strain of 4. Typically, during testing, one of the line contact grips is kept stationary and the opposing line contact grip is moved, but forms where both line contact grips move are also contemplated herein.

The force and actuator displacement data generated during the test are recorded using a Nicolet Integra Model 10, 4-channel 1 Ms/s, 12-bit digitizer oscilloscope with the data acquisition frequency set at 50 kHz. The resulting data are expressed as force (measured in Newtons) versus engineering strain. The engineering strain (c) is dimensionless and is defined as $$\epsilon = \frac{L - L_0}{L_0} = \frac{z}{L_0}$$

where:
$L_0$ is the gauge length (i.e., the distance between lines of grip contact when the undeformed specimen is mounted in the grips). (The $L_0$ in the present example is 3.0 mm.)
L is grip position, the distance between lines of grip contact during the tensile test.
And z is displacement, defined as $z=L-L_0$.

Figure 29:
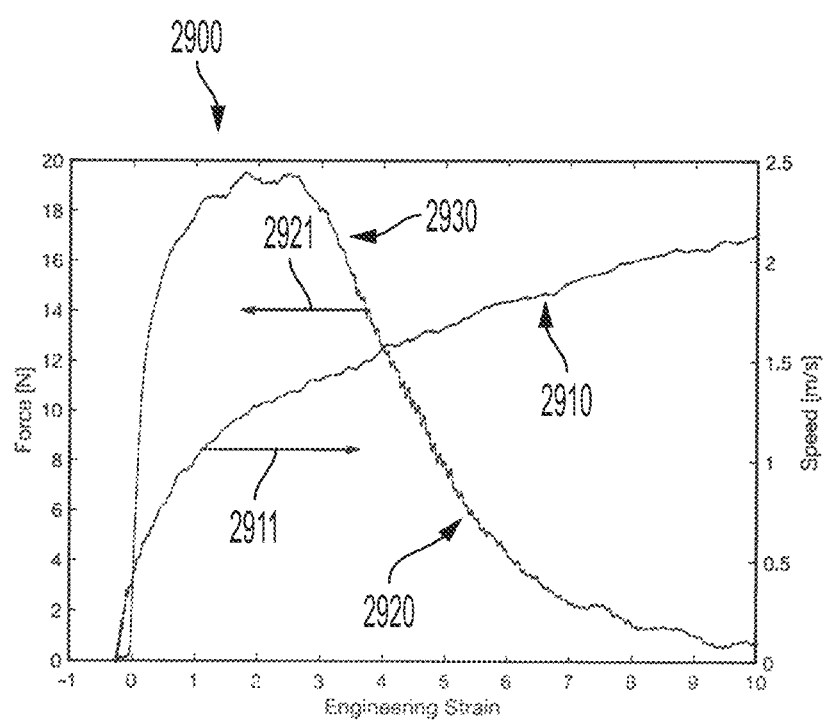
FIG. 29 is a graphical illustration of a suitable deformation regimen for the High Speed Tensile Test herein.

FIG. 29 illustrates a suitable example graph 2900 with two curves 2910 and 2920. The first curve 2910 illustrates a plot of actuator speed (i.e., the relative speed at which one grip is moving away from the other grip) versus engineering strain. The arrow 2911 points to the vertical axis at right used for the plot 2910. The second curve 2920 illustrates a plot of force versus engineering strain and uses the vertical axis at left, as indicated by the arrow 2921. The point of maximum force in the force versus engineering strain plot is identified. Moving toward higher engineering strain, the first point at which the force falls to equal to or less than 90% of the maximum force value is then identified, and the engineering strain at that point is defined as the Extensibility Parameter of the specimen and is recorded to the nearest 0.01. (The region in which this point is found is indicated by arrow 2930.)

The arithmetic mean of the five Extensibility Parameter values determined for each of the five like specimens is reported to the nearest 0.01 as the Extensibility Parameter of the material sample.

Neckdown Modulus Test

Neckdown Modulus is calculated by elongation of a specimen in the machine direction (MD) to multiple specified forces and measuring the cross-direction width at the longitudinal midpoint of the specimen at each of the specified forces. The neckdown modulus is the calculated slope of the resulting force versus width curve.

All testing is performed in a conditioned room maintained at about 23° C.±2 C.° and about 50° C.±2 C.° relative humidity. A clean, smooth, flat, non-sticky, and unobstructed horizontal testing surface (such as a lab bench) that is at least 400 mm wide and 2 m long is required for testing. Force measurements are made using a force gauge with a capacity of 25 N (such as a Medio-Line 40025 available from Pesola AG, Baar, Switzerland) which has been calibrated with weights certified by NIST. Length measurements are made with a NIST traceable ruler that is graduated at 1 mm intervals and longer than the length to be measured. The specimens are pulled using a Plexiglass rod, 9.5 mm diameter and 230 mm long. The ends of a 350 mm long non-stretchable string are attached to each end of the Plexiglass rod. The cut specimens are conditioned lying flat on a horizontal surface under no tension for at least 30 minutes at about 23° C.±2 C.° and about 50° C.±2 C.° relative humidity, prior to testing.

Lay the prepared sample flat on the testing surface. Mark a line on the specimen parallel to the CD, 25 mm from the MD end (MDE1). Mark a second line on the opposite MD edge (MDE2), parallel to the CD, 85 mm from the MDE2. Flip the specimen over so the back side of the specimen is facing upward. Mark a third line on the specimen parallel to the CD, 25 mm from MDE2.

Cut a piece of 2 in. wide duct tape 220 mm±1 mm long. Center the long edge of the tape with the longitudinal centerline of the specimen and align the tape along the marked line such that 25 mm of the tape is applied to the specimen and 25 mm extends past the MDE2. Flip the specimen over so that the back side of the specimen is facing the testing surface once again. Cut a piece of the 2 in wide duct tape approximately 250 mm long. At the MDE1, center the long edge of the tape with the longitudinal centerline of the specimen, and align the tape along the marked line such that 25 mm of the tape is applied to the specimen and 25 mm is applied to the test surface past the MDE1. Place the Plexiglass rod on top of the specimen with it centered along the longitudinal centerline of the specimen and next to the MDE2. Wrap the specimen over the rod and align the distal edge of the tap to the line marked 85 mm from the MDE2. The gage length between the interior edges of tapes is 1320 mm±1 mm. Mark the specimen at the intersection of the longitudinal centerline of the specimen and the middle of the gage length (660 mm±1 mm from either tape edge). Attach the force gauge to the non-stretchable string using a hook fixture.

Align the force gauge width longitudinal centerline of the specimen with minimal slack in the non-stretchable string and specimen. After the test is started, the specimen remains under the applied force for the duration of the experiment. First measure and record the CD width of the specimen at the marked midpoint of the gage to the nearest 0.1 mm.

Manually pull the force gauge at a rate of approximately 100 mm/sec along the projected specimen centerline until the force gauge measures 2.0 N±0.2 N. After 30 sec, measure and record the CD width at the marked midpoint of the gage to the nearest 0.1 mm. Also record the applied force to the nearest 0.01 N. Repeat this measure for every incremental 2 N, with 24 N being the last measured point.

Plot the values of Applied Force (in Newton) versus Specimen CD Width (in m). Neckdown modulus 0-3% is the slope of the line drawn from the origin of the stress-strain curve and intersecting the curve at the 3% elongation point. Report result to the nearest 1 N/m. Repeat the test for five substantially similar specimens and report as the average to the nearest 1 N/m.

Flash Differential Scanning calorimetry (DSC) Test

The Flash Differential Scanning calorimetry (DSC) Test is used to determine the crystallization time of polymer resin under a rapid cooling rate. Suitable instrumentation for this method is the Flash DSC 1 (Mettler-Toledo, Columbus, Ohio, USA) or equivalent rapid scanning, MEMS-chip-based instrumentation.

A specimen is taken from polymer resin in the mass range specified by the rapid-scanning DSC manufacturer (typically between 10 ng and 10 μg). Dry nitrogen is used as the purge gas in the rapid-scanning DSC. The range of testing temperature is set from 25° C. to 230° C. The sample is first heated from ambient temperature to 230° C. at a rate of 0.33° C. per second. The sample is held isothermally at 230° C. for 60 seconds, and it is then cooled from 25° C. to 230° C. at a rate of 100° C./sec. Heat flow as a function of time is measured at a sampling rate of at least $10^4$ samples per second. The time corresponding to the peak in magnitude of measured heat flow versus time is reported as the Time at Peak Maximum and is reported in unit of seconds (s) to the nearest 0.1 ms.

Tape Stripping Test

The Tape Stripping Test is used to determine the Tape Stripping Parameter, which was found to correlate to the incidence of lint production from a nonwoven web thought to be due to fiber breakage.

In the Tape Stripping Test, an article is affixed flatly to a stretch board, which is a piece of rigid material such as polycarbonate to which rows of hook fastening material have been attached such that hook material is able to engage an outer cover of an absorbent article and resist contraction along both the longitudinal and lateral axes of the absorbent article. (The absorbent article is affixed to the stretch board body-facing side away from the stretch board and facing vertically upward with the stretch board being supported by a horizontal rigid surface such as a benchtop.) A piece of 3M Tough Grip Moving Tape (3M Company, Maplewood, Minnesota) approximately 5 cm in width and 25 cm in length is placed on a topsheet of the absorbent article and centered on the topsheet such that the 25 cm dimension of the tape is parallel to a central longitudinal axis of the absorbent article and the 5 cm dimension of the tape is parallel to a central lateral axis of the absorbent article. A 700-gram stainless-steel cylinder (length greater than 5 cm and diameter of approximately 4.1 cm) is freely (with only the gravitation force associated with the mass of the roller providing downward force) rolled over the top of the entire length of the of the tape in four steps: (1) from a front waist end of the absorbent article to a rear waist end, (2) from the rear waist end of the absorbent article to the front waist end, (3) again from the front waist end of the absorbent article to the rear waist end of the absorbent article, and (4) again from the rear waist end of the absorbent article to the front waist end of the absorbent article. The stretch board is then inverted such that the body-facing side of the absorbent article is facing downward (against the rigid horizontal surface). The stainless-steel cylinder is then rolled in the same four-step sequence listed above, this time with the cylinder in immediate contact with the back side of the stretch board. Follow this second sequencing of cylinder rolling, the stretch board is again inverted such that the body-facing side of the absorbent article and tape are facing upward. The tape is peeled from the body-facing surface of the absorbent article at a uniform rate such that the tape is removed in approximately 3 seconds, and an angle of 90° between the peeled tape and the body-facing surface is maintained throughout the peeling process. Generally, some presence of "lint," or nonwoven fibers removed from body facing surface of the absorbent article, is visually discernible.

After the tape is peeled from the absorbent article, it is imaged with a flatbed scanner to enable quantification of the presence of lint on the tape. The tape is held flat with adhesive side up on an Epson Perfection V700 scanner (Seiko Epson Corporation, Tokyo, Japan) or equivalent. The scanner is operated in positive transmission mode, and an image of the tape is captured at 800 dpi and with 16-bit grayscale. All color correction options available in the software are disabled. The resulting image is saved in Tagged Image File Format. If any part of the saved image does not correspond to the tape itself (such as a small margin around the tape), the image is cropped such that the image comprises entirely tape that was in contact with the body-facing surface of the absorbent article.

The saved image is then analyzed further, which can be conveniently facilitated through the use of technical computing software such as MATLAB and the associated Image Processing Toolbox (The Mathworks, Inc, Natick, Massachusetts), or equivalent. The image is first inverted on the 16-bit scale. A threshold value on the 16-bit scale is then determined using the method of Otsu (Otsu, N., "A Threshold Selection Method from Gray-Level Histograms," *IEEE Transactions on Systems, Man, and Cybernetics*, Vol. 9, No. 1, 1979, pp. 62-66.), and this threshold is applied to the image to create a binary image in which the pixels below the threshold are black and correspond to regions of the tape that contain no fibers and pixels above the threshold correspond to fibers captured by the tape. The fraction of pixels in the image that are above the Otsu threshold (that is, that correspond to fibers), is calculated, and this fraction, expressed as a percentage, is recorded as the percent fiber coverage for that absorbent article.

Generally, 10 or more absorbent articles that are nominally identical (like raw material lots, identical process conditions) are analyzed in this way, and the arithmetic mean of the percent fiber coverage among all nominally identical articles analyzed is calculated and reported to the nearest 0.01% as the Percent Fiber Coverage.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a nonwoven topsheet comprising:
      a first nonwoven web comprising:
         continuous multi-component fibers comprising bi-component fibers, wherein a first polymer component comprises polypropylene, wherein the polypropylene has a crystallinity of between about 20% and about 41%, according to a Crystallinity Test, and wherein the polypropylene has a melting temperature of between about 130° C. and about 161° C. according to an Enthalpies of Fusion and Crystallinity Test;
         wherein a second polymer component comprises polyethylene, wherein the polyethylene has a crystallinity of between 45% and about 75% according to a Crystallinity Test, and wherein the polyethylene has a speed of crystallization between about 1300 ms and about 1360 ms according to a Flash DSC Method, and a melting temperature of between about 100° C. and about 140° C. according to an Enthalpies of Fusion and Crystallinity Test;
      wherein the nonwoven topsheet defines a plurality of apertures, and wherein a maximum measurable aperture area equivalent diameter is between about 1.2 mm and about 10 mm, according to an Aperture Area Equivalent Diameter Test;
   a liquid impermeable backsheet; and
   an absorbent core positioned at least partially intermediate the topsheet and the backsheet.

2. The absorbent article of claim 1, wherein the bi-component fibers have a sheath-core configuration comprising a sheath and a core, wherein the sheath comprises the polyethylene, and wherein the core comprises the polypropylene.

3. The absorbent article of claim 1, wherein the first nonwoven web comprises a primary bond area of about 10% to about 35%, according to a Primary Bond Area Test.

4. The absorbent article of claim 1, wherein at least a portion of the plurality of apertures are formed from overbonds, and wherein portions of perimeters of at least some of the apertures comprise a melt lip.

5. The absorbent article of claim 4, wherein the nonwoven topsheet has an extensibility of between about 300% and about 450%, according to a High Speed Tensile Test; and wherein every gram per square meter of nonwoven topsheet has a neckdown modulus of greater than 56 N/m, according to a Neckdown Modulus Test.

6. The absorbent article of claim 1, wherein the nonwoven topsheet has an Effective Open Area of between about 7% and about 30%, according to an Effective Open Area Test.

7. The absorbent article of claim 1, wherein the nonwoven topsheet comprises a second nonwoven web, and wherein the first nonwoven web is hydrophobic.

8. The absorbent article of claim 1, wherein the apertures are non-homogeneous.

9. The absorbent article of claim 1, wherein the nonwoven topsheet comprises three-dimensional features.

10. The absorbent article of claim 1, wherein the nonwoven topsheet has a lint production of between about 3% and about 9%, according to a Tape Stripping Test.

11. A nonwoven web for an absorbent article, the nonwoven web comprising:
    spunbond bi-component fibers, wherein a first polymer component comprises polypropylene, wherein the polypropylene has a crystallinity of between about 20% and about 41%, according to a Crystallinity Test, and wherein the polypropylene has a melting temperature of between about 130° C. and about 161° C. according to an Enthalpies of Fusion and Crystallinity Test; and
    wherein a second polymer component comprises polyethylene, wherein the polyethylene has a crystallinity of between 45% and about 75% according to a Crystallinity Test, and wherein the polyethylene has a speed of crystallization between about 1300 ms and about 1360 ms according to a Flash DSC Method, and has a melting temperature of between about 100° C. and about 140° C. according to an Enthalpies of Fusion and Crystallinity Test.

12. The nonwoven web of claim 11, wherein the spunbond bi-component fibers have a sheath-core configuration comprising a sheath and a core, wherein the sheath comprises the polyethylene, and wherein the core comprises the polypropylene.

13. The nonwoven web of claim 11,
    wherein the nonwoven web has an extensibility of between about 300% and about 450%, according to a High Speed Tensile Test; and
    wherein every gram per square meter of nonwoven web has a neckdown modulus of greater than 56 N/m, according to a Neckdown Modulus Test.

14. The nonwoven web of claim 11, wherein the nonwoven web comprises a plurality of overbonds.

15. The nonwoven web of claim 11, comprising a plurality of nonhomogeneous apertures, wherein the nonwoven web has a maximum measurable aperture area equivalent diameter between about 1.5 mm and about 10 mm, according to an Aperture Area Equivalent Diameter Test.

16. The nonwoven web of claim 15, wherein portions of perimeters of at least some of the apertures comprise a melt lip.

17. The nonwoven web of claim 11, wherein the nonwoven web has an Effective Open Area of between about 7% and about 25%, according to an Effective Open Area Test.

18. The nonwoven web of claim 11, wherein the nonwoven web is joined to a second nonwoven web to form a laminate, wherein the nonwoven web is hydrophobic, wherein the second nonwoven web is hydrophilic, the second nonwoven web comprising second spunbond bi-component fibers comprising a second polypropylene, wherein the second polypropylene has a crystallinity of between about 20% and about 41%, according to the Crystallinity Test, and wherein the second polypropylene has a melting temperature of between about 130° C. and about 161° C.

19. The nonwoven web of claim 11, wherein the nonwoven web has a lint production of between about 3% and about 9%, according to a Tape Stripping Test.

20. An absorbent article comprising:
a nonwoven topsheet comprising:
  a nonwoven web comprising:
    continuous multi-component fibers comprising:
      polypropylene, wherein the polypropylene has a crystallinity of between about 20% and about 41%, according to a Crystallinity Test, and wherein the polypropylene has a melting temperature of between about 130° C. and about 161° C., and polyethylene, wherein the polyethylene reaches a crystallization peak maximum in less than 1360 ms, according to a Flash DSC Method; and
    polyethylene, wherein the polyethylene has a crystallinity of between 45% and about 75% according to a Crystallinity Test, and wherein the polyethylene has a speed of crystallization between about 1300 ms and about 1360 ms according to a Flash DSC Method, and has a melting temperature of between about 100° C. and about 140° C. according to an Enthalpies of Fusion and Crystallinity Test;
  wherein the nonwoven topsheet defines a plurality of apertures, wherein a maximum measurable aperture area equivalent diameter is between about 1.2 mm and about 6 mm, according to an Aperture Area Equivalent Diameter Test, and wherein the nonwoven web has a lint production of between about 3% and about 9%, according to a Tape Stripping Test;
a liquid impermeable backsheet; and
an absorbent core positioned at least partially intermediate the topsheet and the backsheet.

* * * * *